United States Patent
Cholody et al.

(10) Patent No.: US 9,446,021 B2
(45) Date of Patent: *Sep. 20, 2016

(54) DERIVATIVES OF FLUORENE, ANTHRACENE, XANTHENE, DIBENZOSUBERONE AND ACRIDINE AND USES THEREOF

(71) Applicant: Dogwood Pharmaceuticals, Inc., Wilmington, DE (US)

(72) Inventors: Wieslaw M. Cholody, Frederick, MD (US); Yi Zang, Princeton Junction, NJ (US); Karina Zuck, Derwood, MD (US); Jeffrey W. H. Watthey, Frederick, MD (US); Zoe Ohler, Ijamsville, MD (US); Jeffrey Strovel, Laurel, MD (US); Gene Ohler, Ijamsville, MD (US); Sheela Chellappan, Germantown, MD (US); Janak Padia, Germantown, MD (US)

(73) Assignee: Dogwood Pharmaceuticals, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,709

(22) Filed: Jul. 9, 2015

(65) Prior Publication Data

US 2015/0313873 A1 Nov. 5, 2015

Related U.S. Application Data

(62) Division of application No. 13/361,761, filed on Jan. 30, 2012, now Pat. No. 9,120,754, which is a division of application No. 12/451,313, filed as application No. PCT/US2008/006015 on May 9, 2008, now Pat. No. 8,129,519.

(60) Provisional application No. 60/928,592, filed on May 10, 2007, provisional application No. 60/999,153, filed on Oct. 15, 2007.

(51) Int. Cl.
| | |
|---|---|
| A61K 31/395 | (2006.01) |
| A61K 31/4545 | (2006.01) |
| A61K 31/18 | (2006.01) |
| A61K 31/5377 | (2006.01) |
| A61K 31/55 | (2006.01) |
| A61K 31/551 | (2006.01) |
| A61K 31/496 | (2006.01) |
| A61K 31/409 | (2006.01) |
| A61K 31/435 | (2006.01) |
| A61K 31/4709 | (2006.01) |
| A61K 31/4725 | (2006.01) |
| A61K 31/553 | (2006.01) |
| C07C 311/20 | (2006.01) |
| C07D 211/96 | (2006.01) |
| C07D 295/26 | (2006.01) |

(52) U.S. Cl.
CPC ............ *A61K 31/395* (2013.01); *A61K 31/18* (2013.01); *A61K 31/409* (2013.01); *A61K 31/435* (2013.01); *A61K 31/4545* (2013.01); *A61K 31/4709* (2013.01); *A61K 31/4725* (2013.01); *A61K 31/496* (2013.01); *A61K 31/5377* (2013.01); *A61K 31/55* (2013.01); *A61K 31/551* (2013.01); *A61K 31/553* (2013.01); *C07C 311/20* (2013.01); *C07D 211/96* (2013.01); *C07D 295/26* (2013.01); *C07C 2101/14* (2013.01)

(58) Field of Classification Search
CPC .......................... A61K 31/395; C07D 295/26
See application file for complete search history.

(56) References Cited

U.S. PATENT DOCUMENTS

| | | | |
|---|---|---|---|
| 3,627,791 A | 12/1971 | Grisar et al. | |
| 3,714,194 A | 1/1973 | Ulrich | |
| 3,829,578 A | 8/1974 | Fleming et al. | |
| 3,983,248 A | 9/1976 | Grisar et al. | |
| 4,250,097 A * | 2/1981 | Pfister | C07D 311/86 549/393 |
| 5,523,303 A | 6/1996 | Bajnogel et al. | |
| 7,205,311 B2 | 4/2007 | Neidle et al. | |
| 2004/0019042 A1 | 1/2004 | Lee et al. | |
| 2006/0111389 A1 | 5/2006 | Neidle et al. | |

FOREIGN PATENT DOCUMENTS

EP 0307879 B1 6/1994

OTHER PUBLICATIONS

Desai et al., J. Medicinal Chemistry, vol. 49, pp. 1576-1584 (2006).
Grisar et al., J. Medicinal Chemistry, vol. 17, pp. 890-893 (1974).
Massa et al., J. Neuroscience, vol. 26, pp. 5288-5300 (2006).
Blazquez M. Teresa et al., "Acridone heterocycles as fluorescent sensors for anoins", Heterocycles, vol. 69, pp. 73-81 (2006) XP009151241.

* cited by examiner

*Primary Examiner* — Wu-Cheng Winston Shen
*Assistant Examiner* — Christopher R Stone
(74) *Attorney, Agent, or Firm* — Wood, Phillips, Katz, Clark & Mortimer

(57) ABSTRACT

Chemical agents, such as disulfonamide derivatives of fluorene, anthracene, xanthene, dibenzosuberone and acridine, and similar heterocyclic ring structures, including salts thereof, that act as anti-cancer and anti-tumor agents, especially where such agents modulate the activity of the Wnt/β-catenin signaling pathway, and serve to reduce β-catenin levels present in cells, such as cancer cells, or where the agents modulate levels of gene expression in cellular systems, including cancer cells, are disclosed, along with methods for preparing such agents, as well as pharmaceutical compositions containing such agents as active ingredients and methods of using these as therapeutic agents.

15 Claims, No Drawings

DERIVATIVES OF FLUORENE, ANTHRACENE, XANTHENE, DIBENZOSUBERONE AND ACRIDINE AND USES THEREOF

This application is a divisional of U.S. application Ser. No. 13/361,761 filed 30 Jan. 2012, which is a continuation of U.S. application Ser. No. 12/451,313 filed 5 Nov. 2009, which is a national stage of PCT/US2008/006015 filed 9 May 2008 which claims priority to U.S. Provisional Application 60/928,592, filed 10 May 2007, and 60/999,153, filed 15 Oct. 2007, the disclosures of which are herein incorporated by reference in their entirety.

FIELD OF THE INVENTION

The present invention relates to the field of novel compounds useful for the treatment of cancer and methods of use thereof.

BACKGROUND OF THE INVENTION

The Wnt/beta-catenin signaling pathway is recognized as one of the key signaling pathways in cancer and as a valid target for therapeutic intervention in many tumor types, especially colon tumors.

The cells of multicellular organisms have the ability to recognize and signal each other, sometimes from fair distances. Such signaling may be accomplished by production of signaling molecules produced by one cell and which subsequently bind to a specific receptor on a different cell. Such signaling pathways have been implicated in various disease processes, including cancer. Wnt signaling, via receptor binding and subsequent increase in intracellular β-catenin, is referred to as the canonical pathway. Wnt proteins form a family of highly conserved secreted signaling molecules that regulate cell-to-cell interactions and have been implicated in cancer pathogenesis. Wnt proteins bind to receptors of the Frizzled and LRP families on the cell surface. Through several cytoplasmic relay components, the signal is transduced to β-catenin, which then enters the nucleus and forms a complex with TCF to activate transcription of Wnt target genes.

In this pathway, Wnt polypeptides is either present on the surface of a signaling cell or released by that cell and eventually contact a specific cell-surface receptor of another cell. Such receptors on target cells include the Frizzled/LRP receptor (LRP=LDL-receptor-related protein) and they transmit a signal to intracellular proteins, such as β-catenin, whose steady-state level is usually kept relatively low through continuous degradation (usually mediated by proteosomes). This is controlled by a complex containing the proteins GSK-3/APC/Axin (GSK-3=glycogen synthase kinase and APC=Adenomatous Polyposis Coli). The result of Wnt-binding at the surface of the target cell is to inhibit β-catenin degradation, whereupon the latter builds up, enters the nucleus and combines with transcriptional regulators to turn on genes.

It has been found that mutations that promote constitutive activation of the Wnt signaling pathway can lead to cancer. [for a review, see Logan and Nusse, "The Wnt Signaling Pathway in Development and Disease," in *Ann. Rev. Cell Dev. Biol.*, 20:781-810 (2004)] For example, mutations in Axin2 may predispose an individual to colon cancer (Lammi et al., Am. J. Hum. Genet., 74:1043-50 (2004)). In another such example, familial adenomatous polyposis (FAP), an inherited disease characterized by numerous polyps in the colon and rectum, is often caused by truncation of APC (another Wnt signaling-pathway protein), which promotes aberrant activation of the Wnt pathway. [see: Kinzler et al., Science, 253:661-665 (1991)] Mutations in APC and β-catenin have also be detected in colon cancer and other tumor types (for a review see Giles et al., Biochim. Biophys. Acta, 1653:1-24 (2003)). In addition, mutations in Axin that cause loss of function have been identified in hepatocellular carcinomas. [see: Satoh et al., Nat. Genet., 24:245-50 (2000)] Thus, any mutation or other cellular event that serves to decouple Wnt signaling and β-catenin regulation appears to be important in producing cancer.

Because such cancer-genesis events have been linked to elevated levels of β-catenin (i.e., situations where β-catenin levels are Wnt independent), small organic compounds and other agents that serve to re-establish this linkage or otherwise reduce β-catenin would prove useful in abating the cancerous process and find use as anti-neoplastic agents. The present invention provides such agents in the form of disulfonamide derivatives of fluorene, anthracene, xanthene, dibenzosuberone and acridine that reduce levels of beta-catenin in tumor cells.

Structurally related fluorene and anthracene derivatives with the sulfonamide groups substituted with aromatic amines are known in the art (see, for example, US 2004/0019042) as inhibitors of P2X3 and P2X2/3 containing receptors and have been found useful in the treatment and prevention of disorders such as bladder overactivity, urinary incontinence or pain. However, herein it is shown that novel structurally related compounds can be prepared and used as modulators of the Wnt/β-catenin pathway. It is known that β-catenin is a regulator of the Wnt signally pathway. (see Willert and Nusse, Current Opinion in Genetics and Development, 8:95-102 (1998).

BRIEF SUMMARY OF THE INVENTION

The invention provides novel compounds useful for the treatment of cancer that interfere with the Wnt signaling pathway and reduce levels of beta-catenin in cancer cells, and methods for their synthesis. In specific embodiments, these compounds include disulfonamide derivatives of fluorene, anthracene, xanthene, dibenzosuberone and acridine that reduce levels of beta-catenin in tumor cells.

Compounds of the invention have the structure of Formula I:

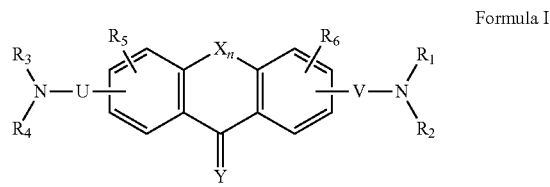

Formula I

Wherein n=0-2 and wherein when n=1, X is selected from $CH_2$, O, $NR_4$, CO, and C=$NOR_4$ and wherein when n=2, X=$CH_2$ Y=O, S, $NOR_A$, or $NR_A$
  wherein $R_A$ is selected from H, alkyl, heteroalkyl, alkenyl, alkynyl, cycloalkyl, —C(=O)$R_B$, —C(=O)O$R_B$, —C(=O)N$R_B R_C$, —C(=N$R_B$)$R_C$, —N$R_B R_C$, heterocycloalkyl, aryl or polyaromatic, heteroaryl, arylalkyl and alkylaryl wherein each of said $R_B$ and $R_C$ is independently H, alkyl, or heteroalkyl, U and V are each independently selected from C=O, and O=S=O and wherein when U is C=O, V is not C=O, $R_1$, $R_2$, $R_3$, and $R_4$ are each independently selected from H, alkyl, heteroalkyl, cycloalkyl, arylcycloalkyl, alkenyl, alkynyl, aryl, heteroaryl, heterocycloalkyl, and each of said $R_1$, $R_2$ and said $R_3$, $R_4$ can independently combine to form heterocycloalkyl, $R_5$ and $R_6$ are each independently selected from H, OH, SH, alkoxy, thioalkoxy, alkyl, halogen, CN, $CF_3$, $NO_2$, $COOR_D$, $CONR_DR_E$, $NR_DR_E$, $NR_DCOR_E$, $NR_DSO_2R_E$, and $NR_FCONR_DR_E$;

wherein $R_D$, $R_E$ and $R_F$ are independently H, alkyl, heteroalkyl, aryl, arylalkyl, heteroaryl, heteroarylalkyl, cycloalkyl, or heterocycloalkyl;

and wherein if X is O, Y is O and U and V are both O=S=O, then $NR_1R_2$ and $NR_3R_4$ are not identical wherein $R_1$ and $R_3$ are each independently selected from H and lower alkyl, and wherein $R_2$ and $R_4$ are each independently selected from lower alkoxy(loweralkyl), di(lower)alkylamino(lower)alkyl, halobenzyl, morpholino(lower)alkyl, or $NR_1R_2$ and $NR_3R_4$ are independently selected from piperidino, morpholino, piperazino, N-phenylpiperazino, ethylamino, or substituted glycine and wherein when X is $(CH_2)_2$ Y is O or NOH, and U and V are each O=S=O then none of $R_1$, $R_2$, $R_3$, and $R_4$ is methyl, and wherein when n=0, Y is O or NOH, and U and V are each O=S=O, then $NR_1R_2$ and $NR_3R_4$ are not identical and $R_1$, $R_2$, $R_3$, and $R_4$ are each independently selected from $C_1$-$C_5$ alkyl, $C_{10}$ alkyl, $C_{16}$ alkyl, $C_{17}$ alkyl, phenyl, benzyl, naphthalenyl, piperazino, pyridinyl, pyrazolyl, benzimidazolyl, triazolyl; or $NR_1R_2$ and $NR_3R_4$ are independently piperidino, morpholino, or piperazino.

and wherein when X is CO, Y is O, and U and V are each O=S=O then $NR_1R_2$ and $NR_3R_4$ are not the same and wherein $R_1$, $R_2$, $R_3$, and $R_4$ are each independently selected from methyl, ethyl, hydroxy-$C_1$-$C_3$-alkyl, SH, RO, COOH, SO, $NH_2$, and phenyl; and $NR_1R_2$ and $NR_3R_4$ are independently selected from unsubstituted piperidino, N-methylpiperazino or N-methylhomopiperazino, and wherein when X is C=O or C=NOH, Y is O or NOH, and U and V are each O=S=O and one of $R_1$ or $R_2$ and one of $R_3$ or $R_4$ is phenyl then the other of $R_1$ or $R_2$ and $R_3$ or $R_4$ is not H or alkyl, including all pharmaceutically acceptable salts, esters, amides, stereoisomers, geometric isomers, solvates or prodrugs thereof.

In specific embodiments, the compounds of the invention include those of Tables 2 to 13 and said compounds make up the invention either individually or in any combination.

The present invention also provides therapeutic compositions of any of the compounds of the invention, such as the compounds of Tables 1 to 13.

The present invention also relates to a method for ameliorating cancer or tumor metastasis in a mammal comprising administering to said mammal an effective amount of a compound of the invention. Especially contemplated are uses of the compounds of Tables 1 to 13.

DEFINITIONS

Unless expressly stated otherwise, each of the following terms has the indicated meaning:

"Acyl" or "carbonyl" is a radical formed by removal of the hydroxy from a carboxylic acid (i.e., R—C(=O)—). Preferred acyl groups include (for example) acetyl, formyl, and propionyl.

The term "carbon chain" embraces any alkyl, alkenyl, alkynyl, or heteroalkyl, heteroalkenyl, or heteroalkynyl group, which are linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

"Alkyl" means a saturated hydrocarbon chain having 1 to 15 carbon atoms, preferably 1 to 10 carbon atoms. Used alone or in combination, it refers to an optionally substituted straight-chain, or optionally substituted branched-chain saturated hydrocarbon radical having from one to about thirty carbons, more preferably one to twelve carbons. Non-limiting examples of alkyl radicals include methyl, ethyl, n-propyl, isopropyl, n-butyl, isobutyl, sec-butyl, tert-butyl, tert-amyl, pentyl, hexyl, heptyl, octyl and the like.

The term "alkenyl," alone or in combination, refers to an optionally substituted straight-chain, or optionally substituted branched-chain hydrocarbon radical having one or more carbon-carbon double-bonds and having from two to about thirty carbon atoms, more preferably two to about eighteen carbons. Examples of alkenyl radicals include ethenyl, propenyl, butenyl, 1,3-butadienyl and the like.

The term "alkynyl," alone or in combination, refers to an optionally substituted straight-chain or optionally substituted branched-chain hydrocarbon radical having one or more carbon-carbon triple-bonds and having from two to about thirty carbon atoms, more preferably from two to about twelve carbon atoms, from two to about six carbon atoms as well as those having from two to about four carbon atoms. Examples of alkynyl radicals include ethynyl, 2-propynyl, 2-butynyl, 1,3-butadiynyl and the like.

"Alkene" is a hydrocarbon chain having at least one (preferably only one) carbon-carbon double bond and having 2 to 15 carbon atoms, preferably 2 to 10, more preferably 2 to 5 carbon atoms.

"Alkyne" is a hydrocarbon chain having at least one (preferably only one) carbon-carbon triple bond and having 2 to 15 carbon atoms, preferably 2 to 10, more preferably 2 to 5 carbon atoms.

Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heteroalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

A "lower alkyl" is a shorter alkyl, e.g., one containing from one to about six carbon atoms.

Also, as referred to herein, a "lower" alkyl, alkene or alkyne moiety (e.g., "lower alkyl") is a chain comprised of 1 to 10, preferably from 1 to 8, carbon atoms in the case of alkyl and 2 to 10, preferably 2 to 8, carbon atoms in the case of alkene and alkyne.

"Alkoxy" means an oxygen radical having a hydrocarbon chain substituent, where the hydrocarbon chain is an alkyl or alkenyl (i.e., —O-alkyl or —O-alkenyl). Examples of alkoxy radicals include methoxy, ethoxy, n-propoxy, isopropoxy, n-butoxy, isobutoxy, sec-butoxy, tert-butoxy, allyloxy and the like.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloalkyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Cycloalkyl" refers to a saturated or unsaturated hydrocarbon ring that is not aromatic. Cycloalkyl rings are monocyclic, or are fused, spiro, or bridged bicyclic or polycyclic ring systems. Monocyclic cycloalkyl rings contain from about 3 to about 12 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, cyclohexyl, cycloheptyl, cyclooctyl and cyclononyl rings.

The term "cycloalkyl" also embraces cyclic alkyl radicals that include monocyclic, bicyclic, tricyclic, and higher polycyclic alkyl radicals wherein each cyclic moiety has from three to about twelve carbon atoms, which would be a 3 to 12 membered ring. Examples of cycloalkyl radicals include cyclopropyl, cyclobutyl, cyclopentyl, cyclohexyl and the like.

The term "cycloalkynyl" refers to cyclic alkynyl radicals which include monocyclic, bicyclic, tricyclic, and higher polycyclic alkynyl radicals wherein each cyclic moiety has from three to about eight carbon atoms. A "lower alkynyl" refers to an alkynyl having from two to about six carbons.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$-$C_{12}$ haloalkyls; more preferred are $C_1$-$C_6$ haloalkyls; still more preferred still are $C_1$-$C_3$ haloalkyls. Preferred halo substituents are fluoro and chloro.

"Heteroatom" is a nitrogen, sulfur, or oxygen atom. Groups containing more than one heteroatom may contain different heteroatoms.

The terms "heteroalkyl, heteroalkenyl and heteroalkynyl" include optionally substituted alkyl, alkenyl and alkynyl structures, as described above, and which have one or more skeletal chain atoms selected from an atom other than carbon, e.g., oxygen, nitrogen, sulfur, phosphorous or combinations thereof.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heteroalkyl, heterocycloalkyl, spirocycle, amino, acylamino, amido, keto, thioketo, cyano, or any combination thereof. Where a group is described, for example, as an alkyl derivative, such as "-ethylpyridine" the dash "-" indicates the point of attachment of the substituent. Thus, "-ethylpyridine" means attachment of ethylpyridine via the ethyl portion of the group whereas "ethylpyridine-" means attachment via the pyridine ring.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heteroalkyl, heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

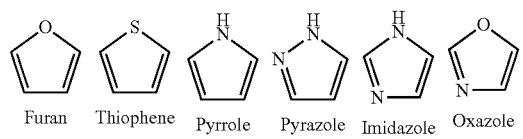

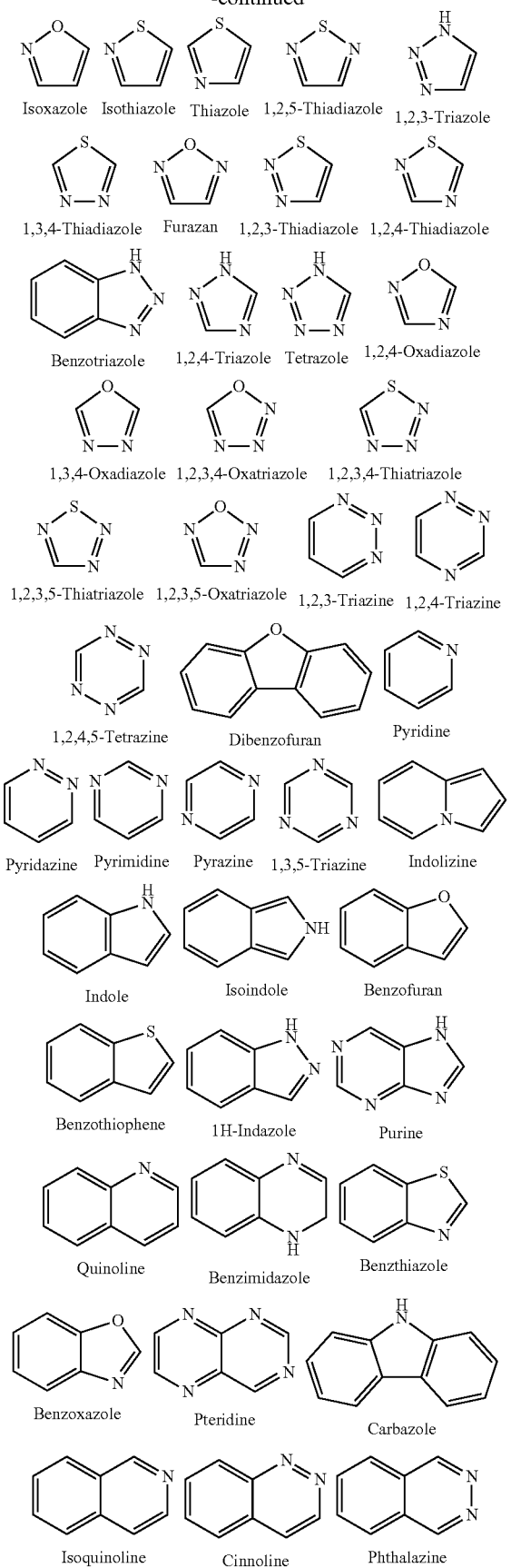

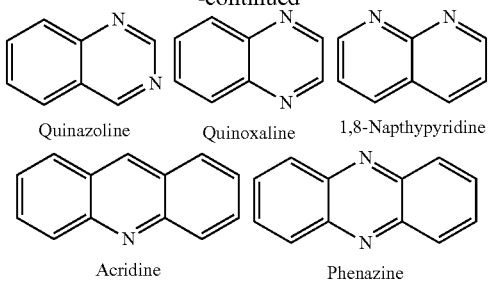

A fused heteroaryl radical may contain from two to four fused rings and where the ring of attachment is a heteroaromatic ring, the other individual rings within the fused ring system may be aromatic, heteroaromatic, alicyclic or heterocyclic. The term heteroaryl also includes mono-heteroaryls or fused heteroaryls having from five to about twelve skeletal ring atoms, as well as those having from five to about ten skeletal ring atoms. The term "lower heteroaryl" refers to a heteroaryl having five to about ten skeletal ring atoms, e.g., pyridyl, thienyl, pyrimidyl, pyrazinyl, pyrrolyl, or furanyl.

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to 4 (preferably 1 to 3) heteroatoms in the ring. Heterocycloalkyl rings are not aromatic. Heterocycloalkyl rings are monocyclic, or are fused, bridged, or Spiro bicyclic ring systems. Monocyclic heterocycloalkyl rings contain from about 3 to about 9 member atoms (including both carbons and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted (i.e., contain hydrogens as substituents of the ring atoms) or substituted (on either carbons or heteroatoms or both) with from 1 to 4 substituents selected from methyl, halo, haloalkyl, cyano, hydroxy, carboxy, keto, thioketo, amino, acylamino, acyl, amido, alkyl (other than methyl), heteroalkyl, haloalkyl, phenyl, alkoxy, aryloxy or any combination thereof. Preferred substituents on heterocycloalkyl include methyl, ethoxyl, halo and haloalkyl. A heterocycloalkyl ring may be attached as a substituent of a larger structure by any chemically feasible atom of said heterocycloalkyl ring. Preferred heterocycloalkyl rings include, but are not limited to, the following:

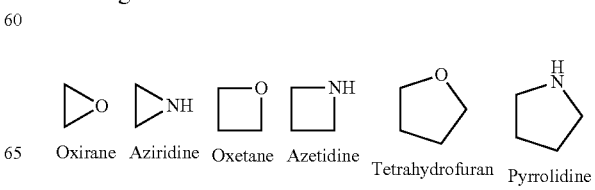

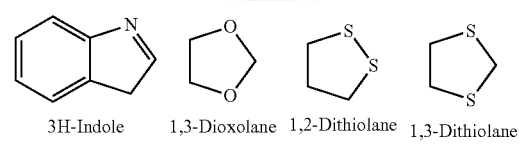

3H-Indole   1,3-Dioxolane   1,2-Dithiolane   1,3-Dithiolane

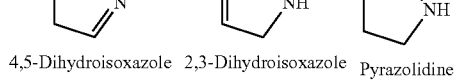

4,5-Dihydroisoxazole   2,3-Dihydroisoxazole   Pyrazolidine

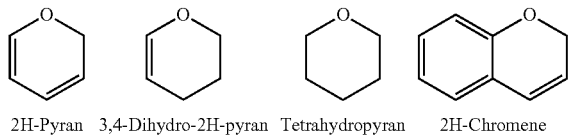

2H-Pyran   3,4-Dihydro-2H-pyran   Tetrahydropyran   2H-Chromene

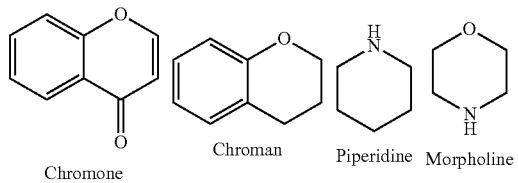

Chromone   Chroman   Piperidine   Morpholine

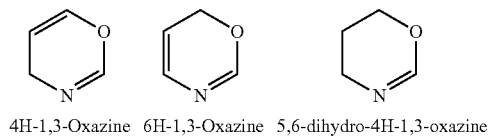

4H-1,3-Oxazine   6H-1,3-Oxazine   5,6-dihydro-4H-1,3-oxazine

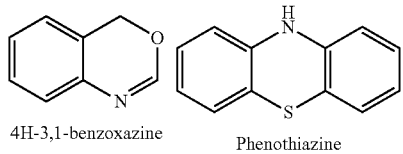

4H-3,1-benzoxazine   Phenothiazine

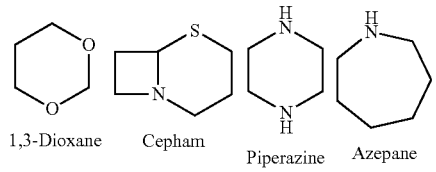

1,3-Dioxane   Cepham   Piperazine   Azepane

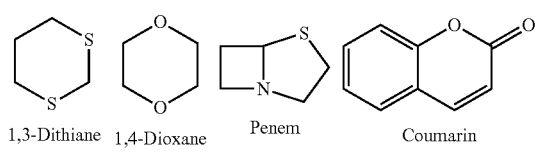

1,3-Dithiane   1,4-Dioxane   Penem   Coumarin

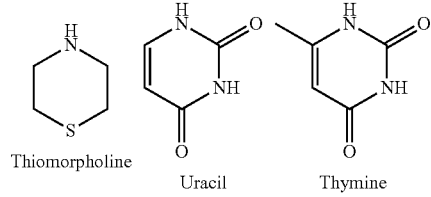

Thiomorpholine   Uracil   Thymine

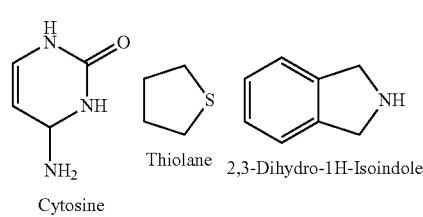

Cytosine   Thiolane   2,3-Dihydro-1H-Isoindole

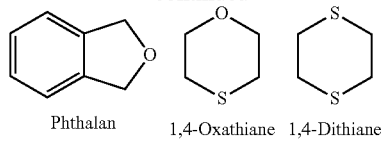

Phthalan   1,4-Oxathiane   1,4-Dithiane

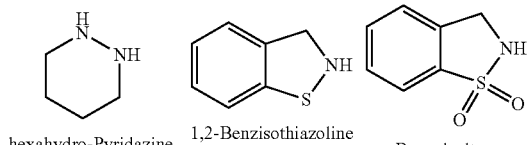

hexahydro-Pyridazine   1,2-Benzisothiazoline   Benzylsultam

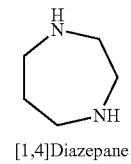

[1,4]Diazepane

The term "membered ring" can embrace any cyclic structure, including aromatic, heteroaromatic, alicyclic, heterocyclic and polycyclic fused ring systems as described below. The term "membered" is meant to denote the number of skeletal atoms that constitute the ring. Thus, for example, pyridine, pyran, and pyrimidine are six-membered rings and pyrrole, tetrahydrofuran, and thiophene are five-membered rings.

The term "aryl," alone or in combination, refers to an optionally substituted aromatic hydrocarbon radical of six to about twenty ring atoms, and includes mono-aromatic rings and fused aromatic ring. A fused aromatic ring radical contains from two to four fused rings where the ring of attachment is an aromatic ring, and the other individual rings within the fused ring may be aromatic, heteroaromatic, alicyclic or heterocyclic. Further, the term aryl includes mono-aromatic ring and fused aromatic rings containing from six to about twelve carbon atoms, as well as those containing from six to about ten carbon atoms. Examples of aryl groups include, without limitation, phenyl, naphthyl, anthryl, chrysenyl, and benzopyrenyl ring systems. The term "lower aryl" refers to an aryl having six to about ten skeletal ring carbons, e.g., phenyl and naphthyl ring systems.

The term "heterocyclic" refers to optionally substituted saturated or unsaturated nonaromatic ring radicals containing from five to about twenty ring atoms where one or more of the ring atoms are heteroatoms such as, for example, oxygen, nitrogen, sulfur, and phosphorus. The term alicyclic includes mono-heterocyclic and fused heterocyclic ring radicals. A fused heterocyclic radical may contain from two to four fused rings where the attaching ring is a heterocyclic, and the other individual rings within the fused heterocyclic radical may be aromatic, heteroaromatic, alicyclic or heterocyclic. The term heterocyclic also includes mono-heterocyclic and fused alicyclic radicals having from five to about twelve skeletal ring atoms, as well as those having from five to about ten skeletal ring atoms. Example of heterocyclics include without limitation, tetrahydrofuranyl, benzodiazepinyl, tetrahydroindazolyl, dihydroquinolinyl, and the like. The term "lower heterocyclic" refers to a heterocyclic ring system having five to about ten skeletal ring atoms, e.g., dihydropyranyl, pyrrolidinyl, indolyl, piperidinyl, piperazinyl, and the like.

The term "alkylaryl," alone or in combination, refers to an aryl radical as defined above in which one H atom is replaced by an alkyl radical as defined above, such as, for example, tolyl, xylyl and the like.

The term "arylalkyl," or "aralkyl," alone or in combination, refers to an alkyl radical as defined above in which one H atom is replaced by an aryl radical as defined above, such as, for example, benzyl, 2-phenylethyl and the like.

The term "heteroarylalkyl" refers to an alkyl radical as defined above in which one H atom is replaced by a heteroaryl radical as defined above, each of which may be optionally substituted but wherein the aryl group is attached to a larger core structure with the alkyl group being the terminal moiety.

The term "alkylheteroaryl" refers to an alkyl radical as defined above in which one H atom is replaced by a heteroaryl radical as defined above, each of which may be optionally substituted but wherein the alkyl group is attached to a larger core structure with the heteroaryl group being the terminal moiety.

The term "aryloxy," alone or in combination, refers to an aryl ether radical wherein the term aryl is defined as above. Examples of aryloxy radicals include phenoxy, benzyloxy and the like.

The term "alkylthio," alone or in combination, refers to an alkylthio radical, alkyl-S—, wherein the term alkyl is as defined above.

The term "arylthio," alone or in combination, refers to an arylthio radical, aryl-S—, wherein the term aryl is as defined above.

The term "heteroarylthio" refers to the group heteroaryl-S—, wherein the term heteroaryl is as defined above.

The term "acyl" refers to a radical —C(O)R where R includes alkyl, alkenyl, alkynyl, aryl, heteroaryl, alicyclic, heterocyclic, arylalkyl or heteroarylalkyl wherein the alkyl, alkenyl, alkynyl, aryl, heteroaryl, alicyclic, heterocyclic, arylalkyl or heteroaryl alkyl groups may be optionally substituted.

The term "acyloxy" refers to the ester group —OC(O)R, where R is H, alkyl, alkenyl, alkynyl, aryl, heteroaryl, alicyclic, heterocyclic, arylalkyl, or heteroarylalkyl wherein the alkyl, alkenyl, alkynyl, aryl, heteroaryl, alicyclic, heterocyclic, arylalkyl or heteroarylalkyl may be optionally substituted.

The term "carboxy esters" refers to —C(O)OR where R is alkyl, aryl or arylalkyl, wherein the alkyl, aryl and arylalkyl groups may be optionally substituted.

The term "carboxamido" refers to the structure —C(O)NRR' where nitrogen is attached to the carbonyl carbon and each of R and R' are independently selected from the group consisting of H, alkyl, aryl, heteroaryl, alicyclic, heterocyclic, arylalkyl and heteroarylalkyl, wherein the alkyl, aryl, heteroaryl, alicyclic, heterocyclic, or arylalkyl groups may be optionally substituted.

The term "oxo" refers to double-bonded oxygen, depicted as =O.

The term "halogen" includes F, Cl, Br and I.

The terms "haloalkyl, haloalkenyl, haloalkynyl and haloalkoxy" include alkyl, alkenyl, alkynyl and alkoxy structures, as described above, that are substituted with one or more fluorines, chlorines, bromines or iodines, or with combinations thereof.

The terms "perhaloalkyl, perhaloalkyloxy and perhaloacyl" refer to alkyl, alkoxy and acyl radicals as described above, that all the H atoms are substituted with fluorines, chlorines, bromines or iodines, or combinations thereof.

The terms "cycloalkyl, arylalkyl, aryl, heteroaryl, alicyclic, heterocyclic, alkyl, alkynyl, alkenyl, haloalkyl, and heteroalkyl" include optionally substituted cycloalkyl, arylalkyl, aryl, heteroaryl, alicyclic, heterocyclic, alkyl, alkynyl, alkenyl, haloalkyl and heteroalkyl groups.

The terms "alkylamino", refers to the group —NHR' where R is independently selected from alkyl.

The terms "dialkylamino", refers to the group —NRR' where R and R' are alkyls.

The term "sulfide" refers to a sulfur atom covalently linked to two atoms; the formal oxidation state of said sulfur is (II). The term "thioether" may be used interchangeably with the term "sulfide."

The term "sulfoxide" refers to a sulfur atom covalently linked to three atoms, at least one of which is an oxygen atom; the formal oxidation state of said sulfur atom is (IV).

The term "sulfone" refers to a sulfur atom covalently linked to four atoms, at least two of which are oxygen atoms; the formal oxidation state of said sulfur atom is (VI).

The terms "optional" or "optionally" mean that the subsequently described event or circumstance may but need not occur, and that the description includes instances where the event or circumstance occurs and instances in which it does not. For example, "aryl optionally mono- or di-substituted with an alkyl" means that the alkyl may but need not be present, or either one alkyl or two may be present, and the description includes situations where the aryl is substituted with one or two alkyls and situations where the aryl is not substituted with an alkyl.

"Optionally substituted" groups may be substituted or unsubstituted. The substituents of an "optionally substituted" group may include, without limitation, one or more substituents independently selected from the following groups or designated subsets thereof: lower alkyl, lower alkenyl, lower alkynyl, lower aryl, heteroaryl, alicyclic, heterocyclic, arylalkyl, heteroarylalkyl, lower alkoxy, lower aryloxy, amino, alkylamino, dialkylamino, diarylalkylamino, alkylthio, arylthio, heteroarylthio, oxo, oxa, carbonyl (—C(O)), carboxyesters (—C(O)OR), carboxamido (—C(O)NH$_2$), carboxy, acyloxy, —H, halo, —CN, —NO$_2$, —N$_3$, —SH, —OH, —C(O)CH$_3$, perhaloalkyl, perhaloalkoxy, perhaloacyl, guanidine, pyridinyl, thiophene, furanyl, indole, indazole, esters, amides, phosphonates, phosphonic acid, phosphates, phosphoramides, sulfonates, sulfones, sulfates, sulphonamides, carbamates, ureas, thioureas and thioamides, thioalkyls. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$).

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well. Further, it is possible using well known techniques to separate the various forms, and some embodiments of the invention may feature purified or enriched species of a given enantiomer or diastereomer.

A "pharmacological composition" refers to a mixture of one or more of the compounds described herein, or pharmaceutically acceptable salts thereof, with other chemical components, such as pharmaceutically acceptable carriers and/or excipients. The purpose of a pharmacological composition is to facilitate administration of a compound to an organism.

The phrase "pharmaceutically acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. A physiologically acceptable carrier should not cause significant irritation to an organism and does not abrogate the biological activity and properties of the administered compound.

The term "excipient" refers to an inert substance added to a pharmacological composition to further facilitate administration of a compound. Examples of excipients include but are not limited to calcium carbonate, calcium phosphate, various sugars and types of starch, cellulose derivatives, gelatin, vegetable oils and polyethylene glycols.

As used herein, the term "therapeutic effect" includes, but is not limited to, the inhibition, in whole or in part, of the growth of cells characteristic of a proliferative disorder, e.g., colon cancer. A therapeutic effect may also include amelioration of one or more of the symptoms of the disease, other than cell growth or size of the cell mass, and may include 1) a reduction in the number of cells; 2) a reduction in cell size; 3) inhibition (i.e., slowing, preferably stopping) of cell infiltration (i.e., metastasis) into peripheral organs; 3) inhibition or slowing of cell growth; and/or 4) relieving one or more symptoms associated with the disease, such as cancer. Any amount or dose of a compound disclosed herein that results in such a therapeutic effect is deemed to be a "therapeutically effective dose" or a "therapeutically effective amount" of said compound.

As it relates to cancer, the phrase "effective amount" means an amount sufficient to effect a desired response, or to ameliorate a symptom or sign, with respect to metastasis or primary tumor progression, size, or growth. Typical mammalian treatment recipients include mice, rats, cats, dogs, and primates, including humans. An effective amount for a particular patient may vary depending on factors such as the condition being treated, the overall health of the patient, the method, route, and dose of administration and the severity of side affects. Preferably, the effect will result in a change in quantitation of at least about 10%, preferably at least 20%, 30%, 50%, 70%, or even 90% or more. When in combination, an effective amount is in ratio to a combination of components and the effect is not limited to individual components alone.

A "solvate" is a complex formed by the combination of a solute (e.g., a metalloprotease inhibitor) and a solvent (e.g., water). See J. Honig et al., The Van Nostrand Chemist's Dictionary, p. 650 (1953).

The terms "optical isomer", "geometric isomer" (e.g., a cis and/or trans isomer), "stereoisomer", and "diastereomer" have the accepted meanings (see, e.g., Hawley's Condensed Chemical Dictionary, 11th Ed.). The illustration of specific protected forms and other derivatives of the compounds of the instant invention is not intended to be limiting. The application of other useful protecting groups, salt forms, prodrugs etc., is within the ability of the skilled artisan.

A "prodrug" is a form of a drug that must undergo chemical conversion by metabolic processes before becoming an active, or fully active, pharmacological agent. A prodrug is not active, or is less active, in its ingested or absorbed or otherwise administered form. For example, a prodrug may be broken down by bacteria in the digestive system into products, at least one of which will become active as a drug. Alternatively, it may be administered systemically, such as by intravenous injection, and subsequently be metabolized into one or more active molecules.

As used herein, the term "$IC_{50}$" refers to an amount, concentration or dosage of a particular test compound that achieves a 50% inhibition of a maximal response in an assay that measures such response. In some method embodiments of the invention, the "$IC_{50}$" value of a compound of the invention can be greater for normal cells than for cells exhibiting a proliferative disorder, e.g., breast cancer cells. The value depends on the assay used.

By a "standard" is meant a positive or negative control. A negative control in the present case refers to a normal as opposed to a cancerous cell, e.g., a sample possessing Wnt/β-catenin pathway activity that correlates with a normal cell. A negative control may also include a sample that contains no such pathway. By contrast, a positive control does contain such pathway, preferably of an amount that correlates with overexpression as found in proliferative disorders, e.g., breast cancers. The controls may be from cell or tissue samples, or else contain purified ligand (or absent ligand), immobilized or otherwise. In some embodiments, one or more of the controls may be in the form of a diagnostic "dipstick."

By "selectively targeting" is meant affecting one type of cell to a greater extent than another, e.g., in the case of cancerous cells versus non-cancerous cells.

DETAILED DESCRIPTION OF THE INVENTION

The present invention provides a compound having the structure of Formula I

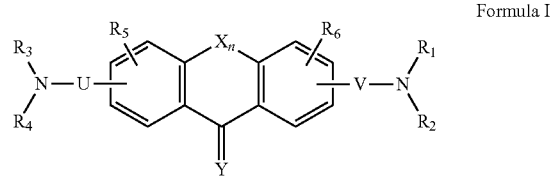

Formula I wherein n=0-2 and wherein when n=1, X is selected from $CH_2$, O, $NR_4$, CO, and C=$NOR_4$ and wherein when n=2, X=$CH_2$ Y=O, S, $NOR_4$, or $NR_4$
  wherein $R_4$ is selected from H, alkyl, heteroalkyl, alkenyl, alkynyl, cycloalkyl, —C(=O)$R_B$, —C(=O)O$R_B$, —C(=O)N$R_B R_C$, —C(=N$R_B$)$R_C$, —N$R_B R_C$, heterocycloalkyl, aryl or polyaromatic, heteroaryl, arylalkyl and alkylaryl
    wherein each of said $R_B$ and $R_C$ is independently H, alkyl, or heteroalkyl, U and V are each independently selected from C=O, and O=S=O and wherein when U is C=O, V is not C=O, R₁, R₂, R₃, and R₄ are each independently selected from H, alkyl, heteroalkyl, cycloalkyl, arylcycloalkyl, alkenyl, alkynyl, aryl, heteroaryl, heterocycloalkyl, and each of said NR₁R₂ and NR₃R₄ can independently form heterocycloalkyl, R₅ and R₆ are each independently selected from H, OH, SH, alkoxy, thioalkoxy, alkyl, halogen, CN, CF₃, NO₂, COOR_D, CONR_DR_E, NR_DR_E, NR_DCOR_E, NR_DSO₂R_E, and NR_FCONR_DR_E;

wherein R_D, R_E and R_F are independently H, alkyl, heteroalkyl, aryl, arylalkyl, heteroaryl, heteroarylalkyl, cycloalkyl, or heterocycloalkyl;

provided that if X is O, Y is O and U and V are both O=S=O, then NR₁R₂ and NR₃R₄ are not identical wherein R₁ and R₃ are each independently selected from H and lower alkyl, and wherein R₂ and R₄ are each independently selected from lower alkoxy(loweralkyl), di(lower)alkylamino(lower)alkyl, halobenzyl, morpholino(lower)alkyl, or NR₁R₂ and NR₃R₄ are independently selected from piperidino, morpholino, piperazino, N-phenylpiperazino, ethylamino, or substituted glycine and that if X is (CH₂)₂, Y is O or NOH, and U and V are each O=S=O then R₁, R₂, R₃, and R₄ are not all methyl and that if n=0, Y is O or NOH, and U and V are each O=S=O, then NR₁R₂ and NR₃R₄ are not identical and of R₁, R₂, R₃ and R₄ are each independently selected from C₁-C₅ alkyl, C₁₀ alkyl, C₁₆ alkyl, C₁₇ alkyl, phenyl, benzyl, naphthalenyl, piperazino, pyridinyl, pyrazolyl, benzimidazolyl, triazolyl; or NR₁R₂ and NR₃R₄ are independently piperidino, morpholino, or piperazino.

and that if X is CO, Y is O, and U and V are each O=S=O then NR₁R₂ and NR₃R₄ are not identical, and wherein R₁, R₂, R₃, and R₄ are each independently selected from methyl, ethyl, hydroxy-C₁-C₃-alkyl, SH, RO, COOH, SO, NH₂, and phenyl or wherein one or both of non-identical NR₁R₂ and NR₃R₄ is unsubstituted piperidino, N-methylpiperazino or N-methylhomopiperazino, and wherein when X is C=O or C=NOH, Y is O or NOH, and U and V are each O=S=O and one of R₁ or R₂ and one of R₃ or R₄ is phenyl then the other of R₁ or R₂ and R₃ or R₄ is not H or alkyl, including all pharmaceutically acceptable salts, esters, amides, stereoisomers, geometric isomers, solvates or prodrugs thereof.

In another embodiment, the invention provides a compound having the structure of Formula II

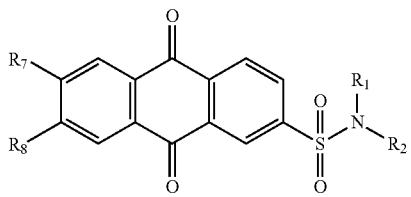

Formula II wherein R₇ and R₈ are independently selected from H and SO₂NR₃R₄ and one of R₇ or R₈ is hydrogen, or of Formula III

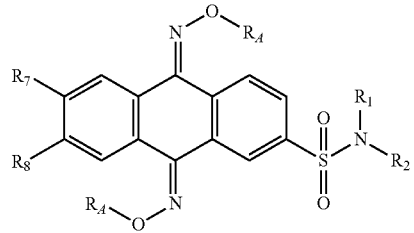

Formula III wherein R₇ and R₈ are independently selected from H and SO₂NR₃R₄, wherein one of R₇ and R₈ is hydrogen and wherein in each of said Formulas II and III the other substituents have the meanings as defined for Formula I.

In specific examples of the invention, the compound of Formula I is a structure wherein A is NR₁ or wherein A is (CR₁R₂)_m, m=1, or wherein A is (CR₁R₂)_m, m=2, and R₁ and R₂ are as defined elsewhere herein.

In specific examples of the invention, the compound of Formula I is a structure wherein B is NR₁, or wherein B is (CR₁R₂)_m, m=1, or wherein B is (CR₁R₂)_m, m=2, and R₁ and R₂ are as defined elsewhere herein.

In other specific examples of the invention, the compound of Formula I is a structure wherein C is NR₁ or wherein C is (CR₁R₂)_m, m=1 or m=2, and R₁ and R₂ are as defined elsewhere herein.

In other specific examples of the invention, the compound of Formula I is a structure wherein D is NR₁ or wherein D is (CR₁R₂)_m, m=1 or m=2, and R₁ and R₂ are as defined elsewhere herein.

In additional specific examples of the invention, the compound of Formula I is a structure wherein n=0, which results in the center X-containing ring being a 5-membered ring.

In other specific examples of the invention, the compound of Formula I is a structure wherein X is O and n=1 or wherein X is O and n=2.

In specific examples of the invention, the compound of Formula I is a structure wherein X is NR₁, n=1, or wherein X is CO and n=1, or wherein X is C=NOR₁, n=1 and R₁ is as defined elsewhere herein.

In specific examples of the invention, the compound of Formula I is a structure wherein X is CR₁R₂, n=1 or wherein X is CR₁R₂, n=2 and wherein R₁ and R₂ are as defined elsewhere herein.

In specific examples of the invention, the compound of Formula I is a structure wherein Y is O, or wherein Y is NR₁ or wherein Y is NOR₁ and wherein R₁ is as defined elsewhere herein.

In one embodiment of Formula I, when Y is O, X is not C=O and when X is C=O, Y is not O. In a separate embodiment, Y is O and X is C=O.

In another embodiment of Formula I, when E is O or NR₁, either Y is not NOH or n is not 1. In a separate embodiment of the latter, when E is O or n is 1 and Y is NOH.

In specific examples of the compounds of Formula I, U and V are each O=S=O. Additional examples of the latter are compounds wherein X is CH₂ and n=1 or 2 and Y is O or S, or compounds wherein X is CH₂ and n=1 or 2 and Y is NOR_A, or NR_A, or compounds X is O, and Y is O or S, or compounds wherein X is O, and Y is NOR_A or NR_A, or compounds wherein X is NR_A, and Y is O or S, or compounds wherein X is NR_A, and Y is NOR_A, or NR_A, or compounds wherein X is CO and Y=O, or compounds wherein X is CO and Y is $NOR_A$ or $NR_A$, or compounds wherein X is $C=NOR_A$ and Y is O, or compounds wherein X is $C=NOR_A$ and Y is $NOR_A$.

In all embodiments of Formula I, when X is C=O or C=NOH, Y is O or NOH, and U and V are each O=S=O and one of $R_1$ or $R_2$ and one of $R_3$ or $R_4$ is phenyl then the other of $R_1$ or $R_2$ and $R_3$ or $R_4$ is not H or alkyl. Thus, by way of non-limiting example, if X is C=O, Y is NOH, U and V are each O=S=O, and $R_1$ and $R_4$ are each phenyl, then $R_2$ is not H or alkyl and $R_3$ is not H or alkyl.

In one embodiment of Formula II, $R_1$, $R_2$, $R_3$, and $R_4$ are each independently selected from H, alkyl, cycloalkyl, alkenyl, and alkynyl. In another such embodiment, $R_A$ is hydrogen and $R_1$, $R_2$, $R_3$, and $R_4$ are each independently selected from H, alkyl, cycloalkyl, alkenyl, and alkynyl. In an additional such embodiment, $NR_1R_2$ and $NR_3R_4$ are each independently a 6- to 15-membered heterocycle, preferably a heterocycloalkyl.

In specific embodiments of Formula II, $R_1$, $R_2$, $R_3$, and $R_4$ are each independently selected from H, alkyl, cycloalkyl, alkenyl, or alkynyl. In other such examples, $R_A$ is hydrogen and $R_1$, $R_2$, $R_3$, and $R_4$ are each independently selected from H, alkyl, cycloalkyl, alkenyl, or alkynyl. In additional examples, $NR_1R_2$ and $NR_3R_4$ are independently 6- to 15-membered heterocycle, preferably a heterocycloalkyl containing one nitrogen in the ring.

In other embodiments, the compounds of the invention are derivatives of one of the following ring systems, especially disulfonamide derivatives thereof:

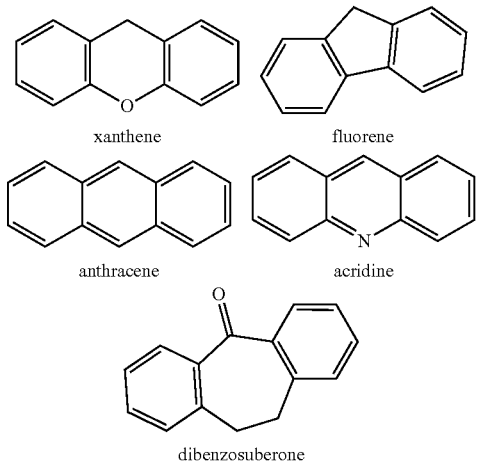

xanthene    fluorene
anthracene    acridine
dibenzosuberone

Such compounds may be suitably substituted.

The present invention also relates to compositions of compounds, including those in Tables 1-13, and having structures of Formula I in a therapeutically effective amount in pharmaceutically acceptable carrier.

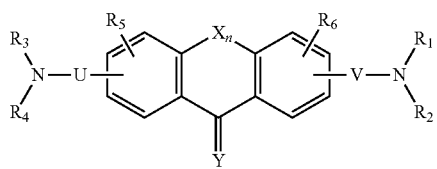

Formula I wherein $X=CH_2$ and n=0-2; or O, $NR_A$, CO, or $C=NOR_A$ and n=1
Y=O, S, $NOR_A$, or $NR_A$
wherein $R_A$ is independently selected from hydrogen, alkyl, heteroalkyl, alkenyl, alkynyl, cycloalkyl, $-C(=O)R_B$, $-C(=O)OR_B$, $-C(=O)NR_BR_C$, $-C(=NR_B)R_C$, $-NR_BR_C$, heterocycloalkyl, aryl or polyaromatic, heteroaryl, arylalkyl and alkylaryl wherein each of said $R_B$ and $R_C$ is independently H, alkyl, heteroalkyl,
U and V are each independently selected from C=O, and O=S=O and provided U is C=O, V can not be C=O,
$R_1$, $R_2$, $R_3$, and $R_4$ are each independently selected from hydrogen, alkyl, heteroalkyl, cycloalkyl, arylcycloalkyl, alkenyl, alkynyl, aryl, heteroaryl, heterocycloalkyl, and each of said $NR_1R_2$ and $NR_3R_4$ can independently form heterocycloalkyl,
$R_5$ and $R_6$ are selected from hydrogen, hydroxyl, sulfhydryl, alkoxy, thioalkoxy, alkyl, halogen, CN, $CF_3$, $NO_2$, $COOR_D$, $CONR_DR_E$, $NR_DR_E$, $NR_DCOR_E$, $NR_DSO_2R_E$, and $NR_FCONR_DR_E$;
wherein $R_D$, $R_E$ and $R_F$ are independently hydrogen, alkyl, heteroalkyl, aryl, arylalkyl, heteroaryl, heteroarylalkyl, cycloalkyl, and heterocycloalkyl;
including all pharmaceutically acceptable salts, esters, amides, stereoisomers, geometric isomers, solvates or prodrugs thereof.

The compounds of said compositions may also contain a multi-ring cycloalkyl or heterocycloalkyl bridge structure (as shown in the tables) containing a total of up to 12 atoms an up to 4 heteroatoms selected from N and O.

The present invention also provides therapeutic compositions of any of the compounds of the invention, such as the compounds of Tables 1 to 13.

The compounds of the invention may be in the form of pharmaceutically acceptable salts, esters, amides, stereoisomers, geometric isomers, solvates or prodrugs thereof. Where a compound of the invention is a stereoisomer, the latter may be an enantiomer or a diastereomer. Where said compound is a enantiomer (or contains a chiral center, for example, a chiral carbon atom), the form of the compound used for pharmaceutical purposes may include either enantiomer or the racemate, although one of said enantiomers may be preferred, such as where it is the active form or is more active than the other enantiomer. Where said compound of the invention is a geometric isomer (e.g., contains a carbon pair with substituents attached in cis- or trans-configuration), either the cis-form, or the trans-form, may be preferred for pharmaceutical use, although mixtures of the cis- and trans-forms may be used in the methods of the invention to the extent they have the desired pharmaceutical effect.

A "pharmaceutically-acceptable salt" is a cationic salt formed at any acidic (e.g., carboxylic acid) group, or an anionic salt formed at any basic (e.g., amino) group. Many such salts are known in the art, as described in WO 87/05297 (Johnston et al., published Sep. 11, 1987 incorporated by reference herein). Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-napthalenesulfonate, nicotinate, nitrate, oxalate; palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Compounds of the present invention that contain one or more acidic functional groups are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of some of the bases that can be used include sodium hydroxide, potassium hydroxide, choline hydroxide, sodium carbonate, $N^+(C_{1-4}\ alkyl)_4$, and the like. Representative organic amines useful for the formation of base addition salts include ethylamine, diethylamine, ethylenediamine, ethanolamine, diethanolamine, piperazine and the like. This invention also envisions the quaternization of any basic nitrogen-containing groups of the compounds disclosed herein. Water or oil-soluble or dispersible products may be obtained by such quaternization.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

In another aspect, the present invention relates to compositions of any of the compounds of the invention, preferably wherein such compound is present in a pharmaceutically acceptable carrier and in a therapeutically effective amount. Such compositions will generally comprise an amount of such compound that is not toxic (i.e., an amount that is safe for therapeutic uses).

Selected examples of compounds of the invention include, but are not limited to, any or all of the compounds of Tables 2-13. Any and all such compounds are specifically claimed for their use in any and all of the methods of the invention. In each indicated structure, the ligand is attached via the atom marked with an asterisk (*). For example, in Table 1 the sulfur atoms of the core structure are attached to the indicated R group at the asterisked nitrogen of the R column of the table.

TABLE 1

| Compound | R | MW |
|---|---|---|
| 1-1 | ethyl piperidine-3-carboxylate (*N) | 646.7 |
| 1-2 | piperidine (*N) | 502.6 |
| 1-3 | 4-methylpiperidine (*N) | 530.6 |
| 1-4 | 3,5-dimethylpiperidine (*N) | 558.7 |
| 1-5 | morpholine (*N) | 506.5 |
| 1-6 | 3-methylpiperidine (*N) | 530.6 |
| 1-7 | *HN-phenyl | 518.5 |
| 1-8 | *HN-2,6-dimethylphenyl | 574.6 |
| 1-9 | azepane (*N) | 530.6 |
| 1-10 | 1,4-diazepane (*N, NH) | 532.6 |
| 1-11 | 4-methyl-1,4-diazepane (*N, N—) | 560.6 |

TABLE 1-continued

[Anthraquinone core with two sulfonyl-R substituents at 2,7-positions]

| Compound | R | MW |
|---|---|---|
| 1-12 | *HN-CH2CH2CH2-N(Et)2 | 592.7 |
| 1-13 | 1-(piperidin-4-ylmethyl)-NHBoc (N-linked piperidine) | 760.9 |
| 1-14 | 1-(piperidin-4-ylmethyl)-NHBoc (N-linked piperidine) | 60.9 |
| 1-15 | 4-(aminomethyl)piperidin-1-yl | 560.6 |
| 1-16 | 4-methylpiperazin-1-yl | 532.6 |
| 1-17 | 4-ethylpiperazin-1-yl | 560.6 |
| 1-18 | 4-acetyl-1,4-diazepan-1-yl | 616.7 |
| 1-20 | 4-ethyl-1,4-diazepan-1-yl | 588.7 |
| 1-21 | piperazin-1-yl | 504.5 |
| 1-22 | *HN-CH2CH2-N(Et)2 | 564.7 |

TABLE 1-continued

[Anthraquinone core with two sulfonyl-R substituents at 2,6-positions]

| Compound | R | MW |
|---|---|---|
| 1-23 | *N(Me)-CH2CH2-N(Et)2 | 592.7 |
| 1-24 | 5-ethyl-2,5-diazabicyclo[2.2.1]heptan-2-yl | 584.7 |
| 1-25 | 4-(2-hydroxyethyl)piperazin-1-yl | 592.6 |
| 1-26 | 4-cyclohexylpiperazin-1-yl | 668.8 |
| 1-27 | azocan-1-yl | 558.7 |
| 1-28 | 4-(2-hydroxyethyl)piperidin-1-yl | 590.7 |
| 1-29 | 1,4-dioxa-8-azaspiro[4.5]decan-8-yl | 618.6 |
| 1-30 | *HN-cyclooctyl | 586.7 |
| 1-31 | *HN-1-adamantyl | 634.8 |
| 1-32 | *HN-2-adamantyl | 634.8 |

TABLE 1-continued

[Structure: anthraquinone with two R-SO2- substituents at 2,7-positions]

| Compound | R | MW |
|---|---|---|
| 1-33 | azonane (9-membered N ring) | 586.7 |
| 1-34 | *HN-CH(CH3)-adamantyl | 690.9 |
| 1-35 | N(cyclohexyl)2 | 694.9 |
| 1-36 | *HN-cyclohexyl-tBu | 642.8 |
| 1-37 | *HN-(4-methylcyclohexyl) | 558.7 |
| 1-38 | *HN-cyclohexyl | 530.6 |
| 1-39 | *HN-cycloheptyl | 558.7 |
| 1-40 | 4-acetylpiperazin-1-yl | 588.6 |
| 1-41 | 3,3-dimethylpiperidin-1-yl | 558.7 |

TABLE 1-continued

[Structure: anthraquinone with two R-SO2- substituents at 2,6-positions]

| Compound | R | MW |
|---|---|---|
| 1-42 | cyclododecyl-N (12-membered N ring) | 670.9 |
| 1-43 | decahydroquinolin-1-yl | 610.7 |
| 1-44 | decahydroisoquinolin-2-yl | 610.7 |
| 1-45 | tricyclic NH* (adamantyl-amine type) | 606.7 |
| 1-46 | 4-phenylpiperidin-1-yl | 654.7 |
| 1-47 | 4-benzylpiperidin-1-yl | 682.8 |
| 1-48 | 4-tert-butylpiperidin-1-yl | 614.8 |
| 1-49 | azecane (10-membered N ring) | 642.8 |
| 1-50 | 4-(piperidine-1-carbonyl)piperidin-1-yl | 724.8 |

TABLE 1-continued

[Structure: anthraquinone with two R-SO2- groups at 2,7 positions]

| Compound | R | MW |
|---|---|---|
| 1-51 | *HN-bornyl (trimethylbicycloheptyl) | 638.8 |
| 1-52 | 4-propylpiperidin-1-yl (*N) | 586.7 |
| 1-53 | decahydroisoquinolin-2-yl (*N) | 610.7 |
| 1-54 | 2-azaspiro[4.5]decan-2-yl (*N) | 610.7 |
| 1-55 | decahydroquinolin-1-yl (*N) | 610.7 |
| 1-56 | 1,4-oxazepan-4-yl (*N) | 534.6 |
| 1-57 | 1-azabicyclo[2.2.2]octane derivative (*N) | 610.7 |
| 1-58 | *HN-pinanyl type | 638.8 |
| 1-59 | 4-tert-butylazepan-1-yl (*N) | 642.8 |

TABLE 1-continued

[Structure: anthraquinone with two R-SO2- groups at 2,6 positions]

| Compound | R | MW |
|---|---|---|
| 1-60 | 1,2,3,4-tetrahydroisoquinolin-2-yl (*N) | 598.6 |
| 1-61 | *HN-CH2CH2-NH-C(=O)-O-tBu | 652.7 |
| 1-62 | *HN-CH2CH2-NH2 | 452.5 |
| 1-63 | *HN-CH2CH2-NH-adamantyl | 720.9 |
| 1-64 | 4,4-diphenylpiperidin-1-yl (*N) | 806.9 |
| 1-65 | *N(CH2CO2Et)-bornyl type | 811.01 |
| 1-66 | *N(4-tert-butylcyclohexyl)(CH2C(=O)OEt) | 815.04 |
| 1-67 | *HN-C(CO2Et)(cyclopentyl) | 646.7 |
| 1-68 | *HN-C(CO2H)(cyclopentyl) | 590.6 |

TABLE 1-continued

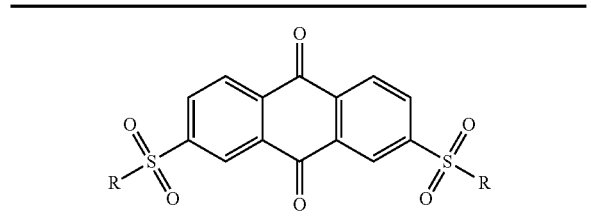

| Compound | R | MW |
|---|---|---|
| 1-69 | N-cyclohexyl(methyl)amino | 558.7 |
| 1-70 | N-(4-tert-butylcyclohexyl)-3-(dimethylamino)propylamino | 816.1 |
| 1-71 | N-(4-tert-butylcyclohexyl)-2-(dimethylamino)ethylamino | 785.1 |
| 1-72 | methyl piperidine-2-carboxylate | 618.6 |
| 1-73 | (6,6-dimethylbicyclo[3.1.1]hept-2-yl)methylamino | 638.8 |
| 1-74 | ethyl N-(6,6-dimethylbicyclo[3.1.1]hept-2-yl)glycinate | 811.01 |

TABLE 1-continued

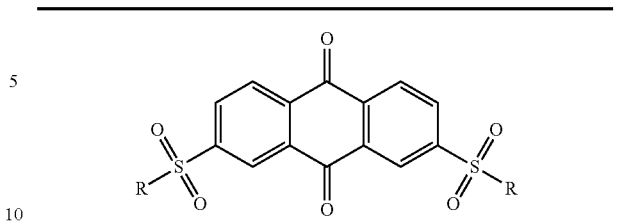

| Compound | R | MW |
|---|---|---|
| 1-75 | N-(6,6-dimethylbicyclo[3.1.1]hept-2-yl)glycine | 754.9 |
| 1-76 | N,N-dipentylamino | 590.7 |
| 1-77 | N,N-diethylamino | 478.5 |
| 1-78 | adamantan-1-ylmethylamino | 662.8 |
| 1-79 | ethyl (2S)-2-amino-4-cyclohexylbutanoate | 758.9 |
| 1-80 | 6,7-dimethoxy-1,2,3,4-tetrahydroisoquinolin-2-yl | 718.7 |
| 1-81 | 2,6-dimethylmorpholin-4-yl | 562.6 |

TABLE 1-continued

[Structure: anthraquinone with two -SO2-R groups at 2,7-positions]

| Compound | R | MW |
|---|---|---|
| 1-82 | 2-propylpiperidin-1-yl | 586.7 |
| 1-83 | *HN-CH2-phenyl (benzylamino) | 546.6 |
| 1-84 | *HN-CH2-cyclohexyl | 558.7 |
| 1-85 | *N(CH2-phenyl)(CH2CH2N(CH3)2) | 688.8 |
| 1-86 | *N(propyl)2 | 534.6 |
| 1-87 | *N(pentyl)2 | 646.9 |
| 1-88 | *N(heptyl)2 | 703.0 |
| 1-89 | *HN-butyl | 478.5 |
| 1-90 | *HN-pentyl | 506.6 |
| 1-91 | *HN-hexyl | 534.6 |
| 1-92 | *HN-CH2CH(CH3)2 (isobutyl) | 506.6 |
| 1-93 | *HN-CH2CH2C(CH3)3 | 534.8 |

TABLE 1-continued

[Structure: anthraquinone with two -SO2-R groups at 2,7-positions]

| Compound | R | MW |
|---|---|---|
| 1-94 | 4-(trifluoromethyl)piperidin-1-yl | 638.5 |
| 1-95 | 1,4,7-trioxa-10-azacyclododecan-10-yl | 682.7 |
| 1-96 | 4-ethoxypiperidin-1-yl | 590.7 |
| 1-97 | 4-(oxiran-2-yl)piperidin-1-yl | 586.6 |
| 1-98 | *HN-(5-methyl-2-oxo-tetrahydropyran-3-yl), t-Bu | 706.8 |

TABLE 2

[Structure: anthraquinone 9,10-dioxime with two -SO2-R groups at 2,7-positions]

| Compound | R | MW |
|---|---|---|
| 2-1 | piperidin-1-yl | 532.6 |
| 2-2 | 4-methylpiperidin-1-yl | 560.6 |
| 2-3 | morpholin-4-yl | 536.5 |

TABLE 2-continued

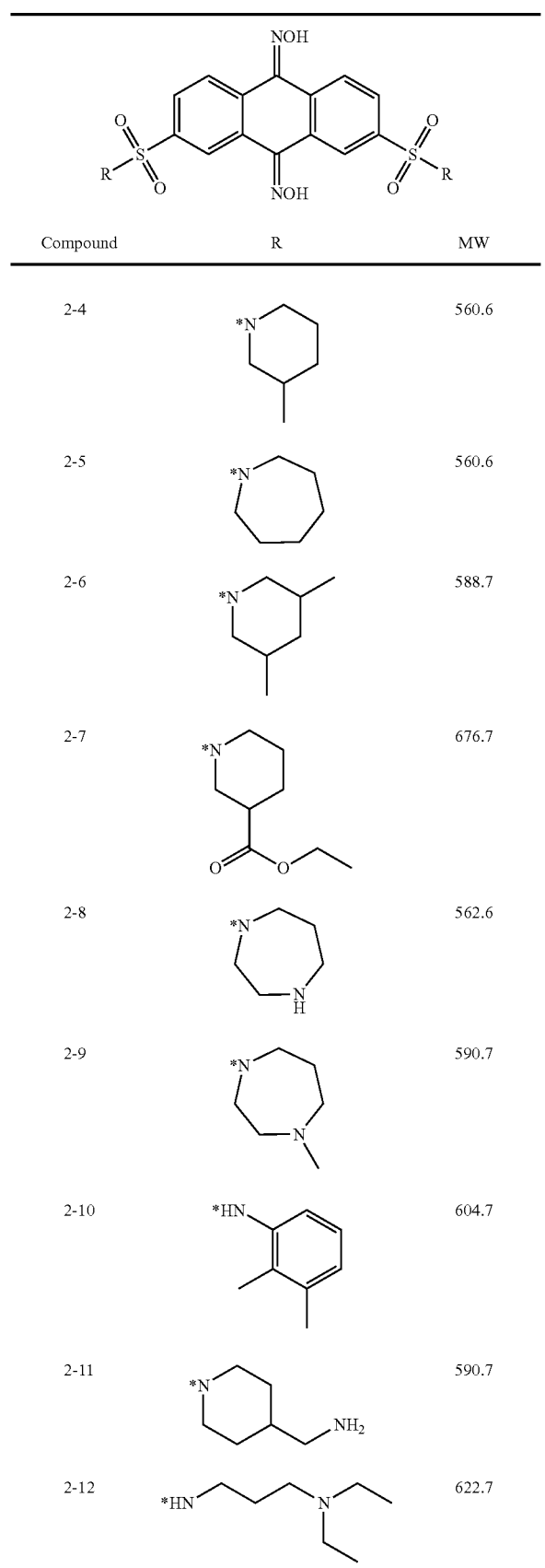

| Compound | R | MW |
|---|---|---|
| 2-4 | 3-methylpiperidinyl | 560.6 |
| 2-5 | azepanyl | 560.6 |
| 2-6 | 3,5-dimethylpiperidinyl | 588.7 |
| 2-7 | ethyl piperidine-3-carboxylate | 676.7 |
| 2-8 | 1,4-diazepanyl | 562.6 |
| 2-9 | 4-methyl-1,4-diazepanyl | 590.7 |
| 2-10 | 2,3-dimethylanilino | 604.7 |
| 2-11 | 4-(aminomethyl)piperidinyl | 590.7 |
| 2-12 | 3-(diethylamino)propylamino | 622.7 |

TABLE 2-continued

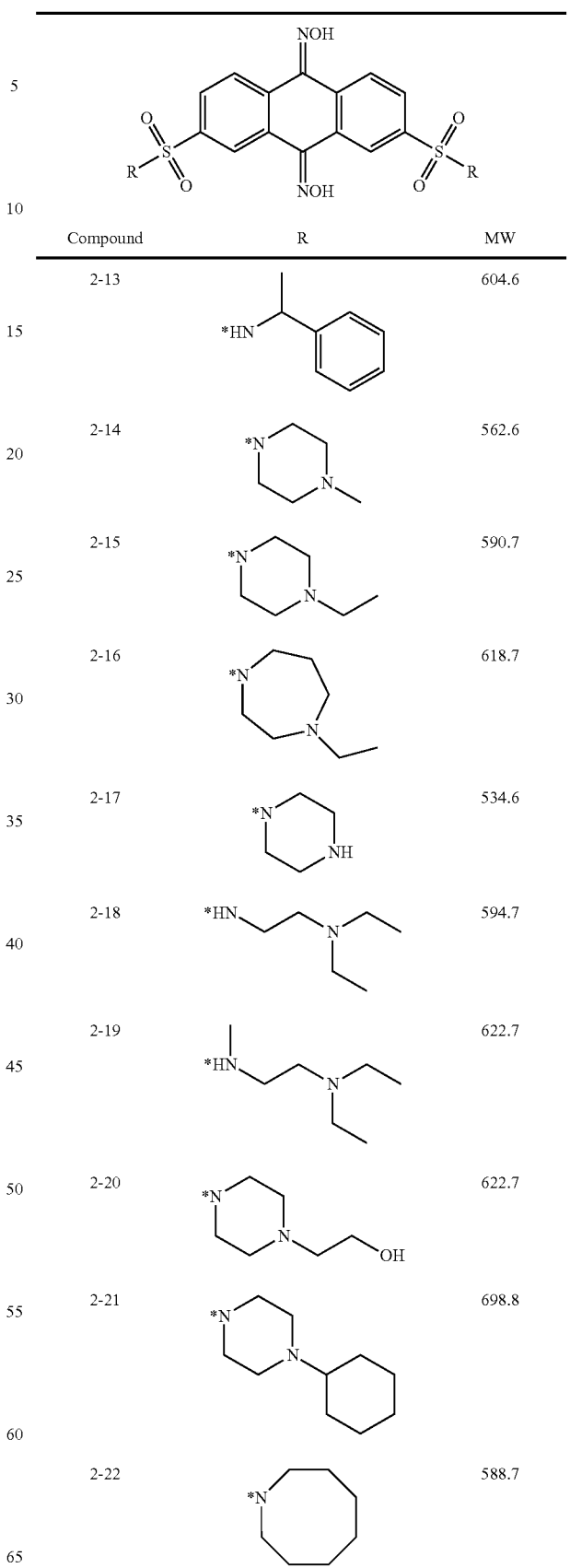

| Compound | R | MW |
|---|---|---|
| 2-13 | 1-phenylethylamino | 604.6 |
| 2-14 | 4-methylpiperazinyl | 562.6 |
| 2-15 | 4-ethylpiperazinyl | 590.7 |
| 2-16 | 4-ethyl-1,4-diazepanyl | 618.7 |
| 2-17 | piperazinyl | 534.6 |
| 2-18 | 2-(diethylamino)ethylamino | 594.7 |
| 2-19 | N-methyl-2-(diethylamino)ethylamino | 622.7 |
| 2-20 | 4-(2-hydroxyethyl)piperazinyl | 622.7 |
| 2-21 | 4-cyclohexylpiperazinyl | 698.8 |
| 2-22 | azocanyl | 588.7 |

TABLE 2-continued

Structure (compounds 2-23 to 2-32):

A dioxime-anthracene core with two sulfonyl (SO₂R) substituents:

R-SO₂–[anthracene-9,10-dione bis(oxime)]–SO₂-R

| Compound | R | MW |
|---|---|---|
| 2-23 | *N-piperidin-4-yl-ethanol (4-(2-hydroxyethyl)piperidin-1-yl) | 620.7 |
| 2-24 | *N-(1,4-dioxa-8-azaspiro[4.5]decan-8-yl) | 648.7 |
| 2-25 | *HN-cyclooctyl | 616.7 |
| 2-26 | *N-azonane (azacyclononyl) | 616.7 |
| 2-27 | NH*-CH(CH₃)-adamantyl (1-(1-adamantyl)ethylamino) | 720.9 |
| 2-28 | *HN-adamantyl (1-adamantylamino) | 664.8 |
| 2-29 | *HN-2-adamantyl | 664.8 |
| 2-30 | *N(cyclohexyl)₂ (dicyclohexylamino) | 724.9 |
| 2-31 | *HN-(4-tert-butylcyclohexyl) | 672.8 |
| 2-32 | *HN-(4-methylcyclohexyl) | 588.7 |

TABLE 2-continued

Structure (compounds 2-33 to 2-41): same dioxime-anthracene bis-sulfonyl core.

| Compound | R | MW |
|---|---|---|
| 2-33 | *HN-cyclohexyl | 560.6 |
| 2-34 | *HN-cycloheptyl | 588.7 |
| 2-35 | *N-(4-Boc-1,4-diazepan-1-yl) (tert-butyl homopiperazine-1-carboxylate) | 762.8 |
| 2-36 | *N-(4-formyl-1,4-diazepan-1-yl) | 618.6 |
| 2-37 | *N-azacyclododecyl (large azacycle) | 700.9 |
| 2-38 | *N-(4-acetyl-1,4-diazepan-1-yl) | 646.7 |
| 2-39 | *N-decahydroquinolin-1-yl | 640.8 |
| 2-40 | *N-decahydroisoquinolin-2-yl | 640.8 |
| 2-41 | *HN-(bicyclo[2.2.1]heptyl / norbornyl) | 636.7 |

TABLE 2-continued

| Compound | R | MW |
|---|---|---|
| 2-42 | 4-phenylpiperidin-1-yl | 684.8 |
| 2-43 | 4-benzylpiperidin-1-yl | 712.8 |
| 2-44 | 4-tert-butylpiperidin-1-yl | 644.8 |
| 2-45 | 3,3-dimethylpiperidin-1-yl | 588.7 |
| 2-46 | azonan-1-yl (nine-membered) | 672.8 |
| 2-47 | 4-(piperidine-1-carbonyl)piperidin-1-yl | 754.9 |
| 2-48 | bornylamino | 668.8 |
| 2-49 | 4-propylpiperidin-1-yl | 616.7 |
| 2-50 | decahydroisoquinolin-2-yl | 640.8 |
| 2-51 | 4,4-dimethylpiperidin-1-yl | 588.7 |

TABLE 2-continued

| Compound | R | MW |
|---|---|---|
| 2-52 | octahydroquinolin-1-yl | 640.8 |
| 2-53 | 1,4-oxazepan-4-yl | 564.6 |
| 2-54 | octahydroisoquinolin-2-yl | 640.8 |
| 2-55 | pinanylamino | 668.8 |
| 2-56 | 4-tert-butylazepan-1-yl | 672.8 |
| 2-57 | 3,4-dihydroisoquinolin-2(1H)-yl | 628.7 |
| 2-58 | N-(adamantan-1-yl)ethane-1,2-diamine | 750.9 |
| 2-59 | 4,4-difluoropiperidin-1-yl | 604.5 |
| 2-60 | dibutylamino | 620.8 |

TABLE 2-continued

| Compound | R | MW |
|---|---|---|
| 2-61 | 4,4-diphenylpiperidin-1-yl | 837.01 |
| 2-62 | 2-azaspiro[4.5]decan-2-yl (8-azaspiro[4.5]decan-8-yl) | 640.8 |
| 2-63 | N-methyl-N-cyclohexylamino | 588.7 |
| 2-64 | 1-aminocyclopentanecarboxylic acid | 620.6 |
| 2-65 | N-(4-tert-butylcyclohexyl)-N-(3-(dimethylamino)propyl)amino | 843.1 |
| 2-66 | N-(4-tert-butylcyclohexyl)-N-(2-(dimethylamino)ethyl)amino | 815.1 |
| 2-67 | ((1S,2R,5S)-6,6-dimethylbicyclo[3.1.1]heptan-2-yl)methylamino | 668.8 |

TABLE 2-continued

| Compound | R | MW |
|---|---|---|
| 2-68 | (S)-piperidine-2-carboxylic acid | 620.6 |
| 2-69 | N,N-diethylamino | 508.6 |
| 2-70 | N-((6,6-dimethylbicyclo[3.1.1]heptan-2-yl)methyl)-N-(carboxymethyl)amino | 784.9 |
| 2-71 | adamantan-1-ylmethylamino | 692.8 |
| 2-72 | (S)-2-amino-4-cyclohexylbutanoic acid | 732.8 |
| 2-73 | (S)-ethyl 2-amino-4-cyclohexylbutanoate | 788.9 |
| 2-74 | N-((6,6-dimethylbicyclo[3.1.1]heptan-2-yl)methyl)-N-(2-(diethylamino)ethyl)amino | 867.2 |

TABLE 2-continued

Structure (compounds 2-75 to 2-82):
Anthracene-9,10-dione dioxime (=NOH at 9,10 positions) with R-SO₂- groups at 2,7 positions.

| Compound | R | MW |
|---|---|---|
| 2-75 | *N-(6,7-dimethoxy-1,2,3,4-tetrahydroisoquinolin-2-yl) | 748.8 |
| 2-76 | *N-(2,6-dimethylmorpholin-4-yl) | 592.6 |
| 2-77 | 2-propylpiperidin-1-yl (*N) | 616.7 |
| 2-78 | *HN-C(COOH)(cycloheptyl) (1-amino-cycloheptanecarboxylic acid) | 676.7 |
| 2-79 | *N-[4-(4-tert-butylcyclohexyl)]-CH₂CH₂-N(Et)₂ | 871.2 |
| 2-80 | *HN-(2,3-dimethylbicyclo[2.2.1]heptyl) | 696.9 |
| 2-81 | *HN-CH₂-phenyl (benzylamino) | 576.6 |
| 2-82 | *HN-CH₂-cyclohexyl | 588.7 |

TABLE 2-continued

Structure (compounds 2-83 to 2-94):
Same anthracene dioxime bis-sulfonamide core.

| Compound | R | MW |
|---|---|---|
| 2-83 | *N(CH₂-phenyl)(CH₂CH₂-N(CH₃)₂) | 718.8 |
| 2-84 | *N(CH₂-pinanyl)(CH₂CH₂CH₂-N(CH₃)₂) | 839.1 |
| 2-85 | *N(n-propyl)₂ | 564.7 |
| 2-86 | *N(n-pentyl)₂ | 676.9 |
| 2-87 | *N(n-hexyl)₂ | 733.03 |
| 2-88 | *HN-n-butyl | 508.6 |
| 2-89 | *HN-n-pentyl | 536.6 |
| 2-90 | *HN-n-hexyl | 564.7 |
| 2-91 | *HN-CH₂CH₂-CH(CH₃)₂ (isoamyl) | 536.6 |
| 2-92 | *HN-CH₂CH₂-C(CH₃)₃ | 564.7 |
| 2-93 | *N-(4-trifluoromethylpiperidin-1-yl) | 668.6 |
| 2-94 | *N-(1-aza-4,7,10-trioxacyclododecane) | 712.7 |

TABLE 2-continued
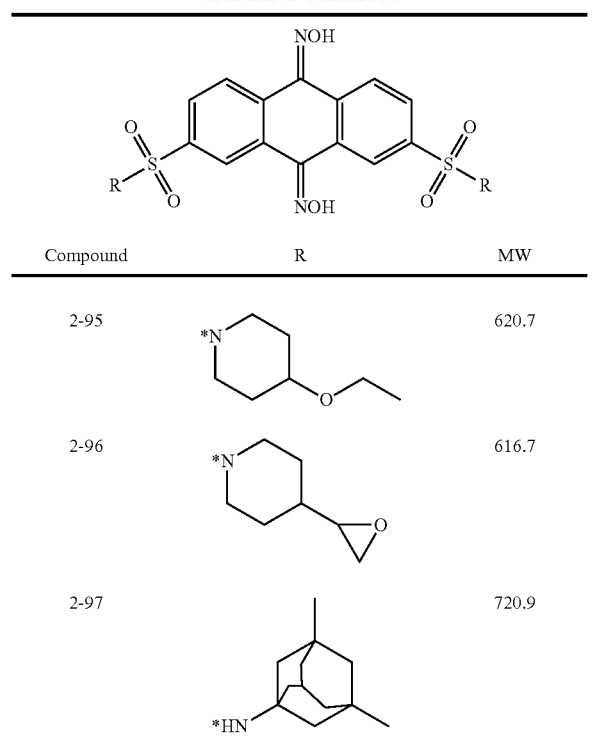
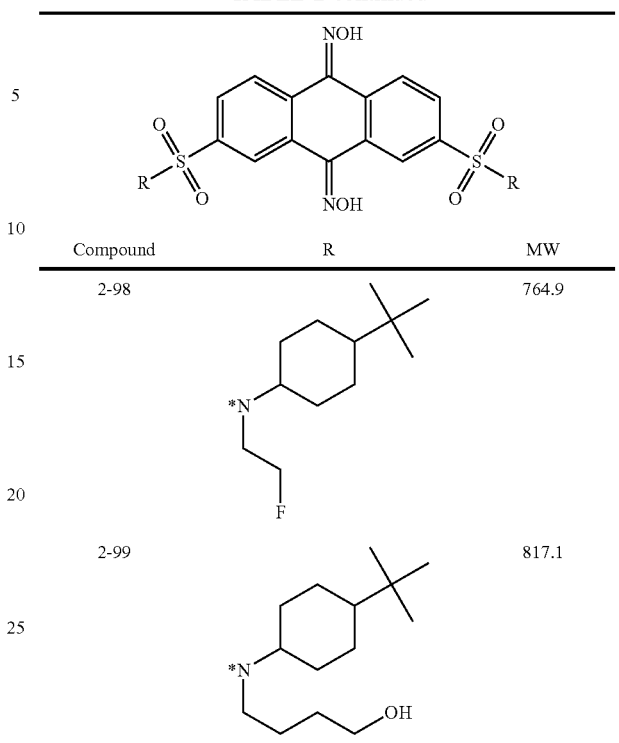
TABLE 3
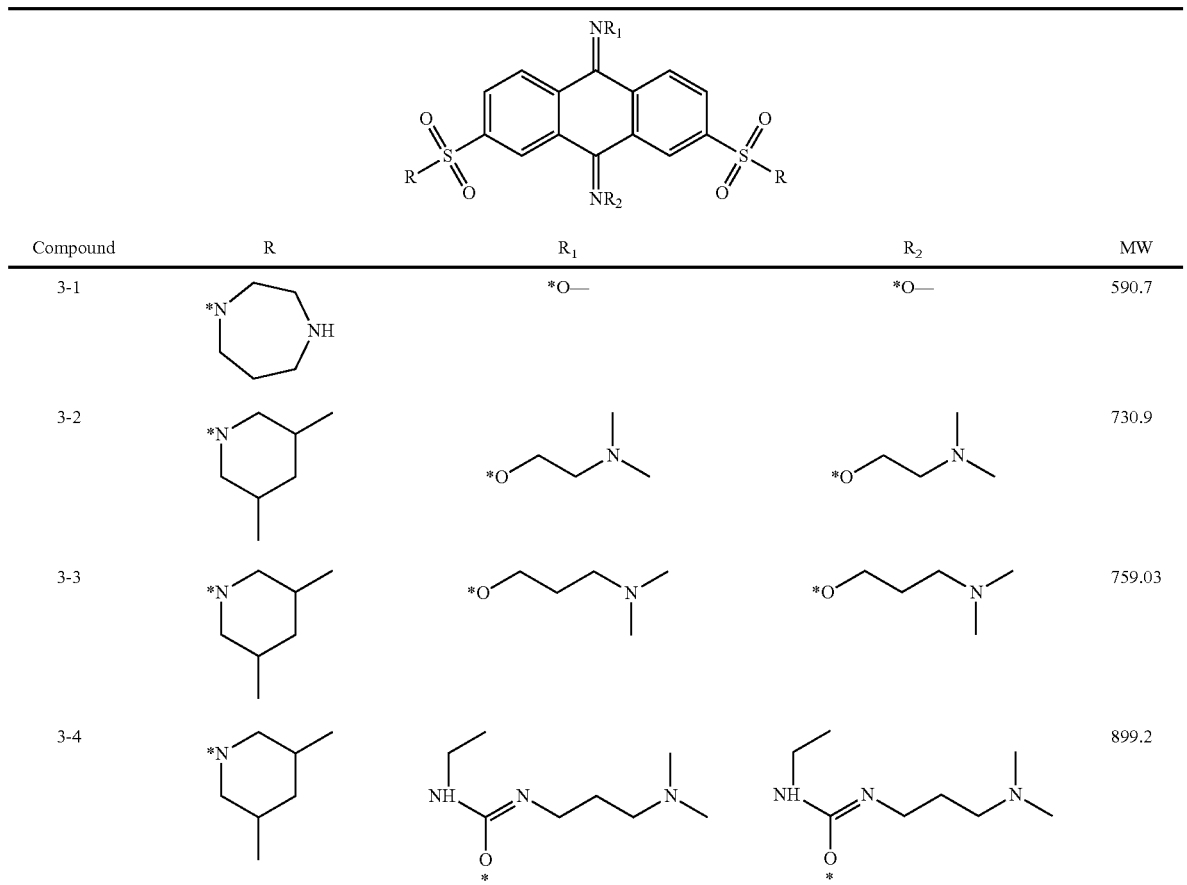

TABLE 3-continued

| Compound | R | R₁ | R₂ | MW |
|---|---|---|---|---|
| 3-5 | N-methylhomopiperazine (*N-CH₂CH₂-N(CH₃)-CH₂CH₂CH₂-) | *O— | *O— | 618.7 |
| 3-6 | azepane (*N-) | *O-CH₂CH₂CH₂-N(CH₃)₂ | *O-CH₂CH₂CH₂-N(CH₃)₂ | 730.9 |
| 3-7 | azepane (*N-) | *O-CH₂CH₂CH₂-N(CH₃)₂ | *O-CH₂CH₂CH₂-N⁺(CH₃)₂-CH₂CH₂CH₂-N(CH₃)₂ | 817.1 |
| 3-8 | azepane (*N-) | *O-CH₂CH₂CH₂CH₂-NH₂ | *O-CH₂CH₂CH₂CH₂-NH₂ | 702.9 |
| 3-9 | azepane (*N-) | *O-CH₂CH₂CH₂-NH₂ | *O-CH₂CH₂CH₂-NH₂ | 674.8 |
| 3-10 | 3,5-dimethylpiperidine | *O-CH₂CH₂-N(pyrrolidine) | *O-CH₂CH₂-N(pyrrolidine) | 783.05 |
| 3-11 | 3,5-dimethylpiperidine | *O-CH₂CH₂-(1-methylpyrrolidin-2-yl) | *O-CH₂CH₂-(1-methylpyrrolidin-2-yl) | 811.1 |
| 3-12 | 3,5-dimethylpiperidine | *O-CH₂CH₂CH₂-N(piperidine) | *O-CH₂CH₂CH₂-N(piperidine) | 839.1 |
| 3-13 | 4-methylpiperidine | *O-CH₂CH₂-N(CH₃)₂ | *O-CH₂CH₂-N(CH₃)₂ | 702.9 |
| 3-14 | 4-methylpiperidine | *O-CH₂CH₂CH₂-N(CH₃)₂ | *O-CH₂CH₂CH₂-N(CH₃)₂ | 730.9 |

TABLE 3-continued

| Compound | R | R₁ | R₂ | MW |
|---|---|---|---|---|
| 3-15 | 4-methylpiperidin-1-yl | *O-CH₂CH₂-pyrrolidin-1-yl | *O-CH₂CH₂-pyrrolidin-1-yl | 755 |
| 3-16 | 4-methylpiperidin-1-yl | *O-CH₂CH₂-(1-methylpyrrolidin-2-yl) | *O-CH₂CH₂-(1-methylpyrrolidin-2-yl) | 783.05 |
| 3-17 | 4-methylpiperidin-1-yl | *O-(CH₂)₃-piperidin-1-yl | *O-(CH₂)₃-piperidin-1-yl | 811.1 |
| 3-18 | azocan-1-yl | *C(O)NH-CH₂CH₃ / N-(CH₂)₃-N(CH₃)₂ | *C(O)NH-CH₂CH₃ / N-(CH₂)₃-N(CH₃)₂ | 899.2 |
| 3-19 | 4-(2-hydroxyethyl)piperidin-1-yl | *C(O)NH-CH₂CH₃ / N-(CH₂)₃-N(CH₃)₂ | *C(O)NH-CH₂CH₃ / N-(CH₂)₃-N(CH₃)₂ | 931.2 |
| 3-20 | 4-methylpiperidin-1-yl | *O-(CH₂)₄-NH₂ | *O-(CH₂)₄-NH₂ | 702.9 |
| 3-21 | 4-methylpiperidin-1-yl | *C(O)NH-CH₂CH₃ / N-(CH₂)₃-N(CH₃)₂ | *C(O)NH-CH₂CH₃ / N-(CH₂)₃-N(CH₃)₂ | 871.1 |
| 3-22 | 1,4-dioxa-8-azaspiro[4.5]dec-8-yl | *C(O)NH-CH₂CH₃ / N-(CH₂)₃-N(CH₃)₂ | *C(O)NH-CH₂CH₃ / N-(CH₂)₃-N(CH₃)₂ | 959.1 |
| 3-23 | azonan-1-yl | *C(O)NH-CH₂CH₃ / N-(CH₂)₃-N(CH₃)₂ | *C(O)NH-CH₂CH₃ / N-(CH₂)₃-N(CH₃)₂ | 927.2 |

TABLE 3-continued
| Compound | R | R₁ | R₂ | MW |
|---|---|---|---|---|
| 3-24 | azocane | *O-propyl-N(CH₃)₂ | *O-propyl-N(CH₃)₂ | 759.03 |
| 3-25 | trans-decahydroisoquinoline | *O-propyl-N(CH₃)₂ | *O-propyl-N(CH₃)₂ | 811.1 |
| 3-26 | azepane | ethyl-NH-C(O)-N-propyl-N(CH₃)₂ | *OH | 715.9 |
| 3-27 | 3,5-dimethylpiperidine | *O-propyl-NH₂ | *OH | 645.8 |
| 3-28 | azocane | *O-propyl-NH₂ | *OH | 645.8 |
TABLE 4
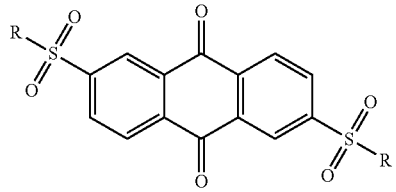
| Compound | R | MW |
|---|---|---|
| 4-1 | piperidin-4-yl-NH-C(O)-O-tBu | 732.6 |
| 4-2 | 3-methylpiperidine | 530.6 |
TABLE 4-continued
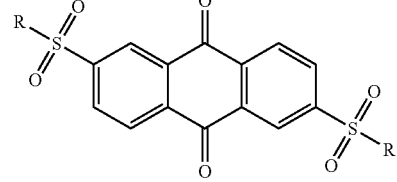
| Compound | R | MW |
|---|---|---|
| 4-3 | 3,5-dimethylpiperidine | 558.7 |
| 4-4 | azepane | 530.6 |

TABLE 4-continued

| Compound | R | MW |
|---|---|---|
| 4-5 | (piperidin-3-yl carboxylic acid ethyl ester) | 646.7 |
| 4-6 | (4-methyl-1,4-diazepan-1-yl) | 560.6 |
| 4-7 | (1,4-diazepan-1-yl) | 532.6 |
| 4-8 | (N,N-diethylethylenediamine) | 564.7 |
| 4-9 | (piperazin-1-yl) | 504.5 |
| 4-10 | (4-ethylpiperazin-1-yl) | 560.6 |
| 4-11 | (5-ethyl-2,5-diazabicyclo[2.2.1]heptan-2-yl) | 584.7 |
| 4-12 | (4-ethyl-1,4-diazepan-1-yl) | 588.7 |
| 4-13 | (azocan-1-yl) | 558.7 |
| 4-14 | (4-methylpiperidin-1-yl) | 530.6 |
| 4-15 | (4,4-dimethylpiperidin-1-yl) | 558.7 |
| 4-16 | (1,3,3-trimethyl-6-azabicyclo[3.2.1]) | 638.8 |
| 4-17 | (4,4-diphenylpiperidin-1-yl) | 806.9 |
| 4-18 | (4-benzylpiperidin-1-yl) | 682.8 |
| 4-19 | (decahydroisoquinolin-2-yl) | 610.7 |
| 4-20 | (3,4-dihydroisoquinolin-2(1H)-yl) | 598.6 |
| 4-21 | (3,3-dimethylpiperidin-1-yl) | 558.7 |
| 4-22 | (thiomorpholin-1-yl) | 538.6 |
| 4-23 | (2,6-dimethylmorpholin-1-yl) | 562.6 |

TABLE 4-continued
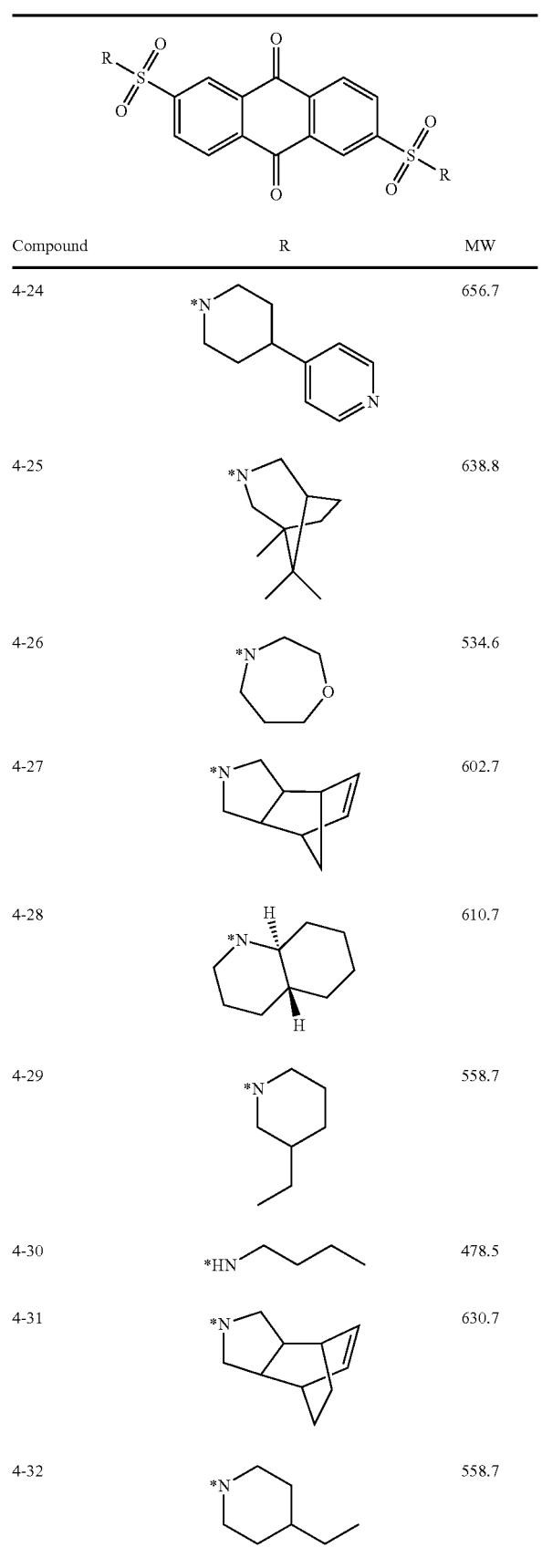
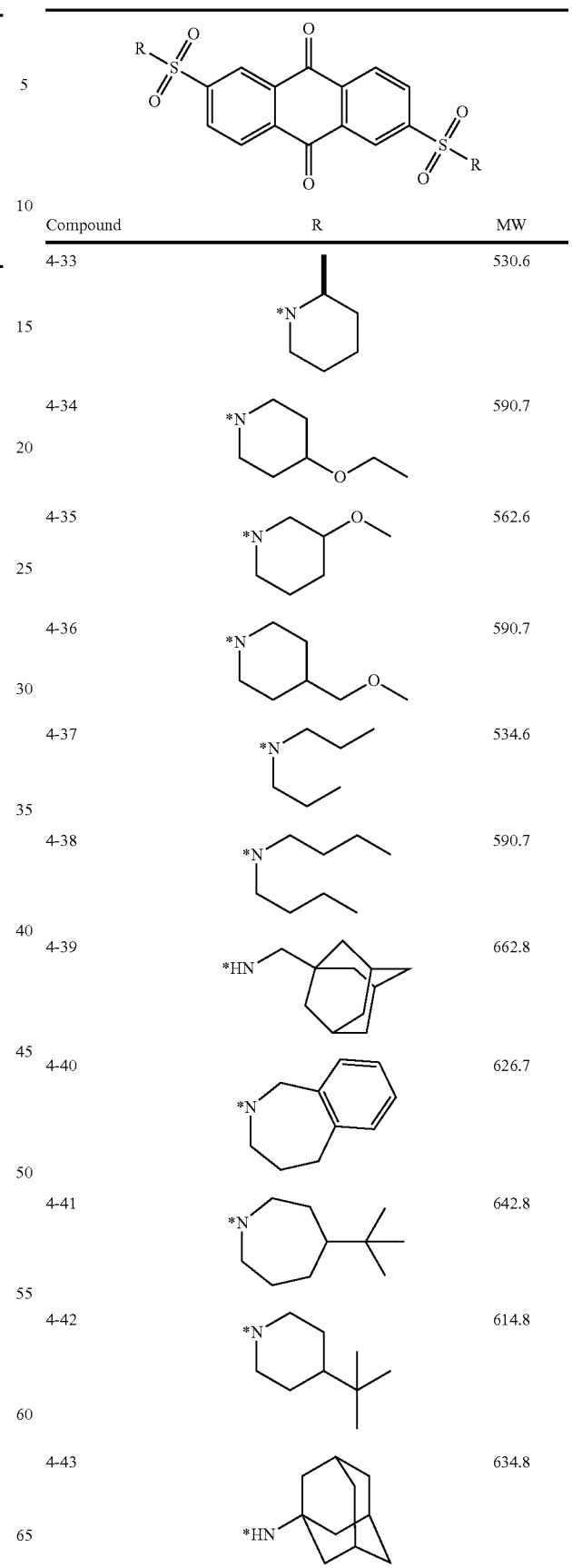

TABLE 4-continued

Structure: anthraquinone-9,10-dione with two R-SO₂- substituents at 2,7 positions

| Compound | R | MW |
|---|---|---|
| 4-44 | *HN-cyclohexyl-tBu | 642.8 |
| 4-45 | 2-azaspiro[5.5]undecane | 638.8 |
| 4-46 | *HN-propyl | 450.5 |
| 4-47 | *HN-pentyl | 506.6 |
| 4-48 | *N-(2,6-dimethylmorpholine) | 562.6 |
| 4-49 | *HN-CH₂-(6,6-dimethylbicyclo[3.1.1]heptyl) | 638.8 |
| 4-50 | 8-ethoxy-2,3,4,9-tetrahydro-1H-pyrido[3,4-b]indol-2-yl | 764.8 |

TABLE 5

Structure: 9,10-bis(hydroxyimino)anthracene with two R-SO₂- substituents at 2,7 positions

| Compound | R | MW |
|---|---|---|
| 5-1 | *N-(3-methylpiperidinyl) | 560.6 |
| 5-2 | *N-(azepanyl) | 560.6 |
| 5-3 | *N-(piperidinyl) | 532.6 |
| 5-4 | *N-(3,5-dimethylpiperidinyl) | 588.7 |
| 5-5 | *N-(piperidin-3-yl ethyl carboxylate) | 676.7 |
| 5-6 | *N-(4-methyl-1,4-diazepanyl) | 590.7 |
| 5-7 | *N-(4-methylpiperidinyl) | 560.6 |
| 5-8 | *N-(4,4-dimethylpiperidinyl) | 588.7 |
| 5-9 | *N-(2-azaspiro[4.5]decanyl) | 640.8 |
| 5-10 | *N-(4-phenylpiperidinyl) | 684.8 |
| 5-11 | *N-(4-tert-butylpiperidinyl) | 644.8 |

TABLE 5-continued

[Structure: anthracene core with =NOH groups at 9,10 positions and two R-SO2- substituents at 2,6 positions]

| Compound | R | MW |
|---|---|---|
| 5-12 | 1,3,3-trimethyl bicyclic amine | 668.8 |
| 5-13 | 3,3-dimethylpiperidinyl | 588.7 |
| 5-14 | azocanyl (8-membered ring) | 588.7 |
| 5-15 | 4,4-diphenylpiperidinyl | 837.01 |
| 5-16 | 4-propylpiperidinyl | 616.7 |
| 5-17 | 4-benzylpiperidinyl | 712.8 |
| 5-18 | adamantyl-NH- | 664.8 |
| 5-19 | 1-(adamantyl)ethyl-NH- | 720.9 |
| 5-20 | decahydroisoquinolinyl | 640.8 |

TABLE 5-continued

[Structure: anthracene core with =NOH groups at 9,10 positions and two R-SO2- substituents (different regiochemistry)]

| Compound | R | MW |
|---|---|---|
| 5-21 | azocanyl | 616.7 |
| 5-22 | 1,2,3,4-tetrahydroisoquinolin-2-yl | 628.7 |
| 5-23 | 1,4-oxazepanyl | 564.6 |
| 5-24 | decahydroquinolinyl | 640.8 |
| 5-25 | 2,6-dimethylmorpholinyl | 592.6 |
| 5-26 | 4-(benzyloxy)piperidinyl | 744.8 |
| 5-27 | 4-(pyridin-4-yl)piperidinyl | 686.8 |
| 5-28 | 3-ethylpiperidinyl | 588.7 |

TABLE 5-continued

| Compound | R | MW |
|---|---|---|
| 5-29 | 4-cyclohexylpiperidin-1-yl | 696.6 |
| 5-30 | 1-methyl-2-azabicyclic | 668.8 |
| 5-31 | aza-crown ether (1,4,7-trioxa-10-azacyclododecyl) | 718.7 |
| 5-32 | *HN-butyl | 508.6 |
| 5-33 | *HN-CH2-adamantyl | 692.8 |
| 5-34 | *N(butyl)2 | 620.8 |
| 5-35 | 4-tert-butylpiperidin-1-yl | 644.8 |
| 5-36 | 1,3-dimethyl-azabicyclic | 668.8 |
| 5-37 | *HN-adamantyl | 664.8 |
| 5-38 | (S)-2-methylpiperidin-1-yl | 560.6 |
| 5-39 | 4-ethoxypiperidin-1-yl | 620.7 |
| 5-40 | 3-methoxypiperidin-1-yl | 592.6 |
| 5-41 | 4-(methoxymethyl)piperidin-1-yl | 620.7 |
| 5-42 | 4-(ethoxymethyl)piperidin-1-yl | 648.7 |
| 5-43 | *N(propyl)2 | 564.7 |
| 5-44 | *HN-(4-tert-butylcyclohexyl) | 672.8 |
| 5-45 | octahydro-pyrrolo-fused bicyclic | 664.8 |
| 5-46 | 2-azaspiro[5.5]undecan-2-yl | 668.8 |

TABLE 6

[Structure: anthracene-9,10-dione bis(oxime) with 2,7-disulfonamide substituents bearing R1, R2 on one side and R1, R3 on the other]

| Compound | R₁ | R₂ | R₃ | MW |
|---|---|---|---|---|
| 6-1 | 4-tert-butylcyclohexyl | H | *-CH₂CH₂-N(CH₃)₂ | 758.1 |
| 6-2 | 4-tert-butylcyclohexyl | H | *-CH₂-N(CH₃)₂ | 744.0 |
| 6-3 | pinanyl | H | *-CH₂CH₂-N(CH₃)₂ | 754.0 |
| 6-4 | 4-tert-butylcyclohexyl | H | *-CH₂-N(CH₂CH₃)₂ | 772.1 |
| 6-5 | pinanyl | H | *-CH₂CH₂-N(CH₃)₂ | 754.0 |
| 6-6 | 4-tert-butylcyclohexyl | H | *-CH₂CH₂-OH | 717.0 |
| 6-7 | 4-tert-butylcyclohexyl | H | *-CH₂-S-CH₂CH₃ | 761.1 |
| 6-8 | 4-tert-butylcyclohexyl | H | *-CH₂CH₂CH₂-CF₃ | 783.0 |
| 6-9 | pinanyl | H | *-CH₂CH₂CH₂-NH₂ | 740.0 |
| 6-10 | 4-tert-butylcyclohexyl | H | *-CH₂CH₂-F | 718.9 |
| 6-11 | 4-tert-butylcyclohexyl | H | *-CH₂CH₂CH₂-OH | 745.0 |

TABLE 7

[Structure: fluoren-9-one with 2,7-bis(sulfonyl-R) substituents]

| Compound | R | MW |
|---|---|---|
| 7-1 | *HN-CH₂-C(=O)OH | 454.4 |
| 7-2 | *HN-C(=O)CH₃ | 422.4 |
| 7-3 | *N-piperazinyl-N'-benzyl | 656.8 |
| 7-4 | *N-piperazinyl-N'-(2-pyridyl) | 630.7 |
| 7-5 | *N-pyrrolidinyl | 446.5 |
| 7-6 | *HN-C₆H₄-NH-C(=O)CH₃ | 604.7 |
| 7-7 | *HN-(CH₂)₉CH₃ | 618.9 |
| 7-8 | *HN-CH(CH₃)-C₆H₅ | 546.7 |
| 7-9 | *HN-(4-pyridyl) | 492.5 |
| 7-10 | *N-(4-methylpiperidinyl) | 502.6 |
| 7-11 | *N-morpholinyl | 478.5 |
| 7-12 | *N-(4-methylpiperazinyl) | 504.6 |
| 7-13 | *HN-CH₂CH₂CH₂CH₃ | 450.6 |

TABLE 7-continued

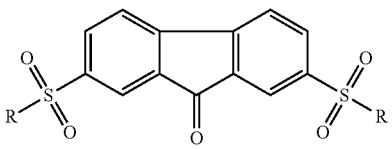

| Compound | R | MW |
|---|---|---|
| 7-14 | *HN-CH(CH3)-Ph (R) | 546.7 |
| 7-15 | *HN-CH(CH3)-Ph (S) | 546.7 |
| 7-16 | *HN-CH2CH2CH2-N(CH3)2 | 508.7 |
| 7-17 | *HN-CH2-(2-furyl) | 498.5 |
| 7-18 | *N-piperidinyl | 474.6 |
| 7-19 | *HN-tBu | 450.6 |
| 7-20 | *HN-C6H4-OMe (4-) | 550.6 |
| 7-21 | *HN-Et | 394.5 |
| 7-22 | *N(CH2CH2OH)2 | 514.6 |
| 7-23 | *HN-C6H4-Me (4-) | 518.6 |
| 7-24 | *N-azepanyl | 502.6 |
| 7-25 | *HN-CH2-Ph | 518.6 |

TABLE 7-continued

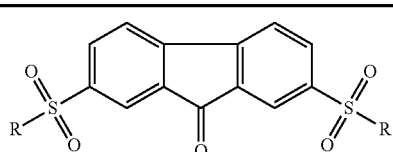

| Compound | R | MW |
|---|---|---|
| 7-26 | *N-piperazinyl-C(O)-(2-furyl) | 664.7 |
| 7-27 | *HN-cyclohexyl | 502.6 |
| 7-28 | *N-(4-OH-4-phenyl-piperidinyl) | 658.8 |
| 7-29 | *N-(4-pyrrolidin-1-yl-piperidinyl) | 612.8 |
| 7-30 | *N-(4-hydroxypiperidinyl) | 506.6 |
| 7-31 | *N-(3-hydroxypiperidinyl) | 506.6 |
| 7-32 | *N-(4-hydroxymethylpiperidinyl) | 534.6 |
| 7-33 | *N-(3-methylpiperidinyl) | 502.6 |
| 7-34 | *N-(2-methylpiperidinyl) | 502.6 |
| 7-35 | *N-(4-(2-hydroxyethyl)piperidinyl) | 562.7 |

TABLE 7-continued
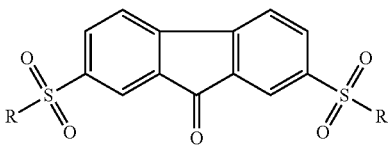
| Compound | R | MW |
|---|---|---|
| 7-36 | 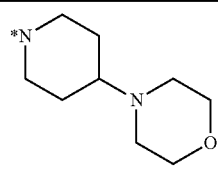 | 644.8 |
TABLE 7-continued
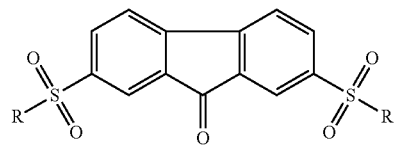
| Compound | R | MW |
|---|---|---|
| 7-37 | 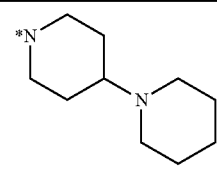 | 640.9 |
TABLE 8
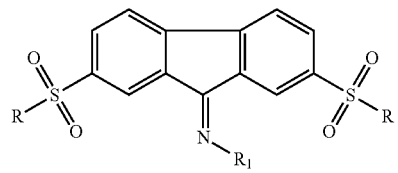
| Compound | R | R₁ | MW |
|---|---|---|---|
| 8-1 |  |  | 451.5 |
| 8-2 | 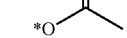 | *OH | 465.6 |
| 8-3 | 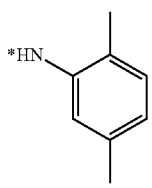 | *OH | 561.7 |
| 8-4 |  | *OH | 489.6 |
| 8-5 | 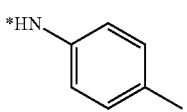 | *OH | 533.6 |
| 8-6 | 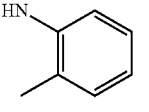 | *OH | 533.6 |
| 8-7 | 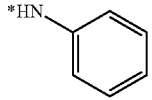 | *OH | 505.6 |
| 8-8 |  | *OH | 409.5 |

TABLE 8-continued
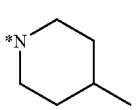
| Compound | R | R₁ | MW |
|---|---|---|---|
| 8-9 | 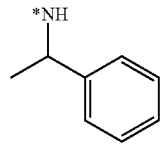 | *OH | 517.7 |
| 8-10 |  | *OH | 561.7 |
| 8-11 | 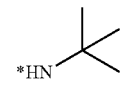 | *OH | 461.6 |
| 8-12 | 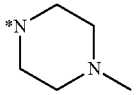 | *OH | 465.6 |
| 8-13 |  | *OH | 519.6 |
| 8-14 | 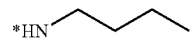 | *OH | 493.6 |
| 8-15 | 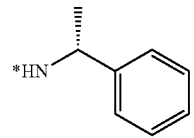 | *OH | 465.6 |
| 8-16 | 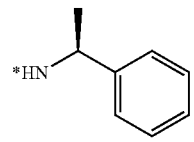 | *OH | 561.7 |
| 8-17 | 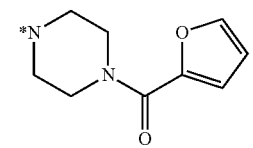 | *OH | 561.7 |
| 8-18 | 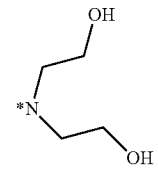 | *OH | 679.7 |
| 8-19 |  | *OH | 619.6 |

TABLE 8-continued
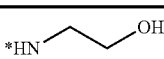
| Compound | R | R₁ | MW |
|---|---|---|---|
| 8-20 | *HN—CH₂CH₂—OH | *OH | 441.5 |
| 8-21 | *N-piperidine | *HN—C(=O)—NH₂ | 531.6 |
| 8-22 | *HN—C₆H₄—OCH₃ (4-methoxyphenyl) | *OH | 565.6 |
| 8-23 | *N-piperazine-N'-(2-pyridyl) | *HN—C(=O)—NH₂ | 687.8 |
| 8-24 | *N-morpholine | *HN—C(=O)—NH₂ | 535.6 |
| 8-25 | NH₂ | *OH | 353.4 |
| 8-26 | *HN—CH₂CH₂—OCH₃ | *OH | 469.5 |
| 8-27 | *N-piperazine-N'-benzyl | *OH | 671.8 |
| 8-28 | *HN—CH₂-(2-furyl) | *HN—C(=S)—NH₂ | 571.6 |
| 8-29 | *N-piperazine-N'-methyl | *HN—C(=O)—NH₂ | 561.7 |
| 8-30 | *HN—C(CH₃)₂—CH₂OH | *OH | 497.6 |
| 8-31 | *N(CH₃)—CH₂CH₂—OH | *OH | 469.5 |
| 8-32 | *O-(2-naphthyl) | *OH | 607.6 |
| 8-33 | NH₂* | *HN—C₆H₅ | 428.5 |

TABLE 8-continued

| Compound | R | R₁ | MW |
|---|---|---|---|
| 8-34 | *NH-(1-naphthyl) | *OH | 605.7 |
| 8-35 | *O-(2-chlorophenyl) | *OH | 576.4 |
| 8-36 | *HN-CH₂-phenyl | *OH | 533.6 |
| 8-37 | *HN-cyclohexyl | *OH | 517.7 |
| 8-38 | *N-azepane | *OH | 517.7 |
| 8-39 | *N-(4-hydroxy-4-phenylpiperidine) | *OH | 673.8 |
| 8-40 | *N-(4-pyrrolidin-1-yl-piperidine) | *OH | 627.8 |
| 8-41 | *N-(4-hydroxypiperidine) | *OH | 521.6 |
| 8-42 | *N-(3-hydroxypiperidine) | *OH | 521.6 |
| 8-43 | *N-(4-hydroxymethylpiperidine) | *OH | 549.7 |

TABLE 8-continued

| Compound | R | R₁ | MW |
|---|---|---|---|
| 8-44 | 3-methylpiperidin-1-yl | *OH | 517.7 |
| 8-45 | 2-methylpiperidin-1-yl | *OH | 517.7 |
| 8-46 | 4-(2-hydroxyethyl)piperidin-1-yl | *OH | 577.7 |
| 8-47 | piperidin-1-yl | *OMe | 503.6 |
| 8-48 | 4-methylpiperidin-1-yl | *OMe | 531.7 |
| 8-49 | 4-morpholinopiperidin-1-yl | *OH | 659.8 |
| 8-50 | [1,4'-bipiperidin]-1'-yl | *OH | 655.9 |
| 8-51 | pyrrolidin-1-yl | *OMe | 475.6 |
| 8-52 | 3,5-dimethylpiperidin-1-yl | *OH | 545.7 |
| 8-53 | 3,5-dimethylpiperidin-1-yl | *OMe | 559.7 |

TABLE 8-continued

| Compound | R | $R_1$ | MW |
|---|---|---|---|
| 8-54 | [*N-piperidine-3-C(O)O-ethyl] | *OH | 633.7 |
| 8-55 | [*HN-C(O)-O-tBu] | *OH | 719.9 |
| 8-56 | [*N-piperidine-4-NH2] | *OH | 519.6 |
| 8-57 | [*N-piperidine-4-methyl] | *OH | 518.6 |
| 8-58 | [*HN-(CH2)3-N(Et)2] | *OH | 579.8 |
| 8-59 | [*N-piperidine-3-COOH] | *OH | 577.6 |
| 8-60 | [*N-piperidine-4-CH2NH2] | *OH | 547.7 |
| 8-61 | [*N-piperidine-4-C(O)O-ethyl] | *OH | 633.7 |
| 8-62 | [*N-piperidine-2-C(O)O-ethyl] | *OH | 633.7 |
| 8-63 | [*N-piperidine-4-COOH] | *OH | 577.6 |

TABLE 8-continued
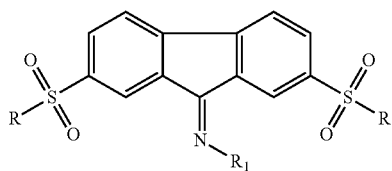
| Compound | R | R₁ | MW |
|---|---|---|---|
| 8-64 | piperidin-4-yl-C(O)NH₂ | *OH | 575.7 |
| 8-65 | piperidin-3-yl-C(O)NH(CH₂)₃N(CH₃)₂ | *OH | 745.9 |
| 8-66 | piperidin-3-yl-C(O)NHCH₂CH₂NH₂ | *OH | 661.8 |
| 8-67 | piperidin-3-yl-C(O)NH(CH₂)₃N(CH₃)₂ | *OH | 830.1 |
| 8-68 | piperidin-3-yl-C(O)NHEt | *OH | 631.8 |
| 8-69 | piperidin-3-yl-C(O)NHCH₂CH₂OH | *OH | 663.8 |
| 8-70 | piperidin-3-yl-C(O)NH₂ | *OH | 575.7 |
| 8-71 | 4-methyl-1,4-diazepan-1-yl | *OH | 547.7 |
| 8-72 | 3,5-dimethylpiperidin-1-yl | *OCH₂CH₂N(CH₃)₂ | 616.8 |

TABLE 8-continued

[Structure: fluorene core with two sulfonyl-R groups and =N-R₁]

| Compound | R | R₁ | MW |
|---|---|---|---|
| 8-73 | 3,5-dimethylpiperidinyl (*N) | *O-CH₂CH₂-N⁺(CH₃)₂-propyl | 688.9 |
| 8-74 | 3,5-dimethylpiperidinyl (*N) | *O-propyl-N(CH₃)₂ | 630.9 |
| 8-75 | azepanyl (*N) | *O-CH₂CH₂-N(CH₃)₂ | 588.8 |
| 8-76 | azepanyl (*N) | *O-CH₂CH₂-N⁺(CH₃)₂-propyl | 660.9 |
| 8-77 | azepanyl (*N) | *O-CH₂-CH(CH₃)-CH₂-N(CH₃)₂ | 644.9 |
| 8-78 | azepanyl (*N) | *OH | 545.7 |

TABLE 9

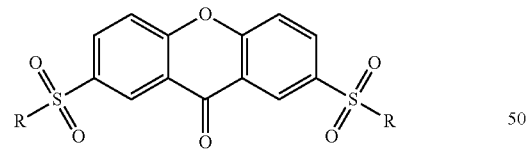

| Compound | R | MW |
|---|---|---|
| 9-1 | 4-methylpiperidinyl | 518.6 |
| 9-2 | piperidine-3-carboxylic acid ethyl ester | 634.7 |

TABLE 9-continued

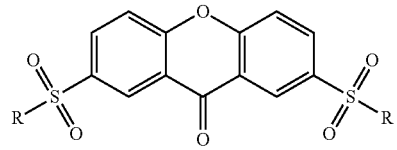

| Compound | R | MW |
|---|---|---|
| 9-3 | piperidine-3-carboxylic acid | 578.6 |
| 9-4 | piperidinyl | 490.6 |

TABLE 9-continued
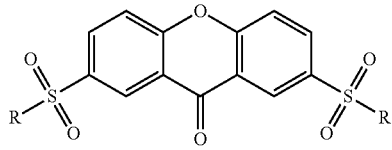
| Compound | R | MW |
|---|---|---|
| 9-5 | 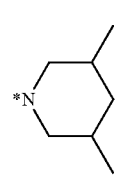 | 518.6 |
| 9-6 | 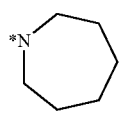 | 546.7 |
| 9-7 | 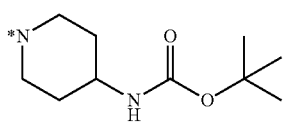 | 518.6 |
| 9-8 | 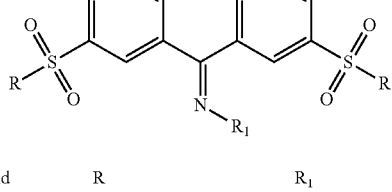 | 720.9 |
TABLE 10
| Compound | R | R₁ | MW |
|---|---|---|---|
| 10-1 | 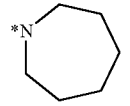 | *OH | 533.7 |
| 10-2 | *N(piperidine) | *OH | 505.6 |
| 10-3 | 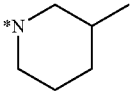 | *OH | 533.7 |
| 10-4 | 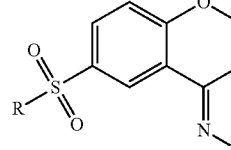 | *OH | 533.7 |
TABLE 10-continued
| Compound | R | R₁ | MW |
|---|---|---|---|
| 10-5 | 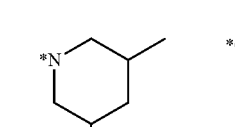 | *OH | 561.7 |
| 10-6 | (3,5-dimethylpiperidine) | *O-CH₂CH₂-N(CH₃)₂ | 632.8 |
| 10-7 | (3,5-dimethylpiperidine) | *O-CH₂CH₂-N⁺(CH₃)₂-CH₂CH₂-N(CH₃)₂ | 704.9 |
| 10-8 | (3,5-dimethylpiperidine) | *-CH₂CH₂-N(CH₃)₂ | 616.8 |
| 10-9 | (3,5-dimethylpiperidine) | *O-CH₂CH₂CH₂-NH₂ | 618.8 |
TABLE 11
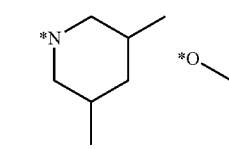
| Compound | R | R₁ | MW |
|---|---|---|---|
| 11-1 | 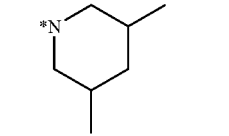 | Me | 531.7 |
| 11-2 | 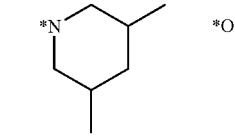 | H | 517.7 |

TABLE 11-continued

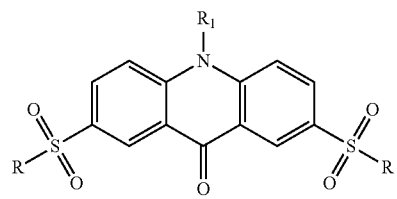

| Compound | R | R₁ | MW |
|---|---|---|---|
| 11-3 | 3,5-dimethylpiperidinyl | H | 545.7 |
| 11-4 | 3,5-dimethylpiperidinyl | Me | 559.7 |
| 11-5 | homopiperazinyl (NH) | Me | 533.7 |
| 11-6 | homopiperazinyl (NBoc) | H | 719.9 |
| 11-7 | homopiperazinyl (NH) | H | 519.6 |

TABLE 12

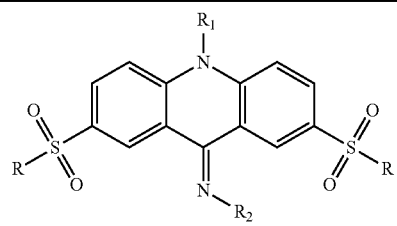

| Compound | R | R₁ | R₂ | MW |
|---|---|---|---|---|
| 12-1 | azepanyl | Me | *OH | 546.7 |
| 12-2 | azepanyl | H | *OH | 532.7 |

TABLE 12-continued

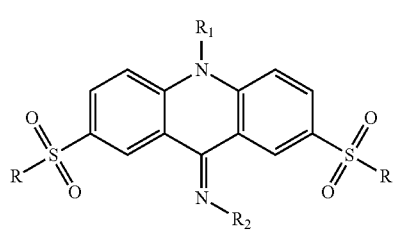

| Compound | R | R₁ | R₂ | MW |
|---|---|---|---|---|
| 12-3 | 3,5-dimethylpiperidinyl | H | *OH | 560.7 |
| 12-4 | 3,5-dimethylpiperidinyl | Me | *OH | 574.8 |
| 12-5 | 3,5-dimethylpiperidinyl | Me | *CH₂CH₂N(Me)₂ | 643.9 |
| 12-6 | 3,5-dimethylpiperidinyl | H | *CH₂CH₂N(Et)₂ | 643.9 |

TABLE 13

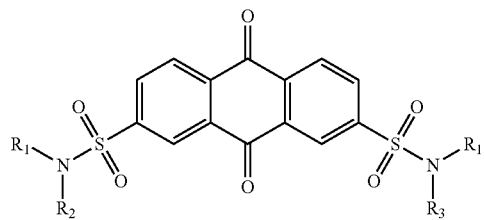

| Compound | R₁ | R₂ | R₃ | MW |
|---|---|---|---|---|
| 13-1 | 4-tert-butylcyclohexyl | H | *CH₂CH₂N(Me)₂ | 728.0 |
| 13-2 | 4-tert-butylcyclohexyl | H | *CH₂N(Me)₂ | 714.0 |

TABLE 13-continued

Structure: anthraquinone-2,7-disulfonamide with R1, R2 on one nitrogen and R1, R3 on the other.

| Compound | R1 | R2 | R3 | MW |
|---|---|---|---|---|
| 13-3 | (pinane/bicyclic group with H stereochemistry) | H | *—CH2CH2—N(CH3)2 | 724.0 |
| 13-4 | *—cyclohexyl-C(CH3)3 (4-tert-butylcyclohexyl) | H | *—CH2CH2—N(Et)2 | 742.1 |
| 13-5 | *—(pinanyl) | H | *—CH2CH2—N(CH3)2 | 724.0 |
| 13-6 | *—4-tert-butylcyclohexyl | H | *—CH2CH2—OH | 686.9 |
| 13-7 | *—4-tert-butylcyclohexyl | H | *—CH2—S—CH2CH3 | 731.1 |
| 13-8 | *—4-tert-butylcyclohexyl | H | *—CH2CH2—CF3 | 753.0 |
| 13-9 | *—(pinanyl) | H | *—CH2CH2CH2—NH2 | 710.0 |
| 13-10 | *—4-tert-butylcyclohexyl | H | *—CH2CH2—F | 688.9 |
| 13-11 | *—4-tert-butylcyclohexyl | H | *—CH2CH2CH2—OH | 715.0 |

TABLE 14

| Gene No. | Gene Name |
|---|---|
| 1 | Activating transcription factor 3 |
| 2 | AHNAK nucleoprotein 2 |
| 3 | Aldo-keto reductase family 1, member C2 (dihydrodiol dehydrogenase 2; bile acid binding protein; 3-alpha hydroxysteroid dehyd |
| 4 | Basic helix-loop-helix domain containing, class B, 2 |
| 5 | CD200 molecule |
| 6 | Chemokine (C-C motif) ligand 20 |
| 7 | Chromosome 13 open reading frame 15 |
| 8 | Cytidine deaminase |
| 9 | Dehydrogenase/reductase (SDR family) member 9 |
| 10 | DNA-damage-inducible transcript 3 |
| 11 | DnaJ (Hsp40) homolog, subfamily B, member 9 |
| 12 | DnaJ (Hsp40) homolog, subfamily C, member 12 |
| 13 | Dopa decarboxylase (aromatic L-amino acid decarboxylase) |
| 14 | Dual specificity phosphatase 1 |
| 15 | Dual specificity phosphatase 5 |
| 16 | Epithelial membrane protein 3 |
| 17 | GABA(A) receptor-associated protein like 1 |
| 18 | GABA(A) receptors associated protein like 3 |
| 19 | Growth differentiation factor 15 |
| 20 | GTP binding protein overexpressed in skeletal muscle |
| 21 | Helicase, lymphoid-specific |
| 22 | Heme oxygenase (decycling) 1 |
| 23 | Histone cluster 2, H2be |
| 24 | hypothetical protein MGC14376 |
| 25 | IL8 |
| 26 | Interferon stimulated exonuclease gene 20 kDa |
| 27 | Interleukin 32 |
| 28 | Interleukin 8 |
| 29 | Laminin, alpha 3 |
| 30 | Lysosomal trafficking regulator |
| 31 | NADPH oxidase 1 |
| 32 | Optineurin |
| 33 | Protein phosphatase 1, regulatory (inhibitor) subunit 15A |
| 34 | PTEN induced putative kinase 1 |
| 35 | Ras homolog gene family, member F (in filopodia) |
| 36 | Sclerostin domain containing 1 |
| 37 | Sequestosome 1 |
| 38 | Small proline-rich protein 1A |
| 39 | Small proline-rich protein 1B (cornifin) |
| 40 | Small proline-rich protein 3 |
| 41 | Solute carrier family 7, (cationic amino acid transporter, y + system) member 11 |
| 42 | SPC25, NDC80 kinetochore complex component, homolog (*S. cerevisiae*) |
| 43 | S-phase kinase-associated protein 2 (p45) |
| 44 | Tubulin, alpha 1a |

In accordance with the foregoing, the present invention is directed to use of the compounds of the invention as active ingredients for medicaments, in particular for medicaments useful for the treatment of tumors. The compounds of the invention will thus be present in pharmaceutical compositions containing compounds of Formulas I or II as active ingredients, in admixture with pharmaceutically acceptable vehicles and excipients, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., N.J. current edition). Use of such carriers is well known to those skilled in the art and will not be discussed further herein.

Also in accordance with the foregoing, the present invention relates to a method for preventing or treating a disease associated with a change in levels of expression of particular sets of genes in a mammal comprising administering to said mammal an effective amount of a compound of the invention.

Compounds according to the present invention will have the effect of reducing size and number of tumors, especially primary tumors, in a mammal, especially a human, in need of such treatment. A statistically significant change in the numbers of primary tumor or metastasizing cells will typically be at least about 10%, preferably 20%, 30%, 50%, 70%, 90%, or more.

In accordance with the present invention, the agents described herein may be combined with other treatments of the medical conditions described herein, such as other chemotherapies, radiation treatments, immunotherapy, surgical treatments, and the like. The compounds of the invention may also be administered in combination with such other agents as painkillers, diuretics, antidiuretics, antivirals, antibiotics, nutritional supplements, anemia therapeutics, blood clotting therapeutics, bone therapeutics, and psychiatric and psychological therapeutics.

Determination of the appropriate treatment dose is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects.

The specific dose of compound administered according to this invention to obtain therapeutic and/or prophylactic effect will, of course, be determined by the particular circumstances surrounding the case, including, for example, the specific compound administered, the route of administration, the condition being treated, and the individual being treated. A typical daily dose (administered in single or divided doses) will contain a dosage level of from about 0.01 mg/kg to about 50-100 mg/kg of body weight of an active compound of the invention. Preferred daily doses generally will be from about 0.05 mg/kg to about 25 mg/kg and ideally from about 0.1 mg/kg to about 10 mg/kg. Factors such as clearance rate, half-life and maximum tolerated dose (MTD), while not specifically recited herein, may be readily determined by one of ordinary skill in the art using standard procedures.

An effective amount of a therapeutic will modulate the symptoms typically by at least about 10%; usually by at least about 20%; preferably at least about 30%; or more preferably at least about 50%. Alternatively, modulation of migration will mean that the migration or trafficking of various cancer cell types is affected. Such will result in, e.g., statistically significant and quantifiable changes in the numbers of cells being affected. This may be a decrease in the numbers of target cells being attracted within a time period or target area. Rate of primary tumor progression, size, or growth may also be monitored.

In another aspect, the present invention relates to a method for preventing or treating a disorder modulated by altered gene expression, wherein the disorder is selected from the group consisting of cancer, cardiovascular disorders, arthritis, osteoporosis, inflammation, periodontal disease and skin disorders, comprising administering to a mammal in need of such treatment or prevention a therapeutically effective amount of a compound of the invention.

In a preferred embodiment, the present invention relates to a method of preventing, treating or ameliorating cancer or tumor metastasis in a mammal comprising administering to said mammal an effective a compound of the invention, preferably where said mammal is a human.

The compounds of the invention will commonly exert a therapeutic effect by modulation of one or more genes found in a cell, especially a mammalian cell, such as a cancer cell, preferably colon cancer and most preferably adenocarcinoma. Thus, a compound, or compounds, of the invention can be used to determine or demarcate a set of genes by determining modulation of such set of genes by one or more compounds of the invention. For example, where a set of genes is found to be up regulated in cancer cells versus otherwise normal cells, especially normal cells of the same tissue or organ as the cancer cells, a set of genes can be determined by their common property of being modulated (based on a change in expression of the genes, such as a change in rate or amount of RNA transcribed or the amount of polypeptide produced by said expression) by contacting such genes, or a cell containing such genes, with one or more of the compounds of the invention. The extent of such modulation may, of course, be related to the amount of said compound, or compounds, used in the contacting. Such modulation may include the increased expression of all the determined genes (i.e., the genes of the set), the decreased expression of all genes of the set, or the increase in expression of some of the genes of the set and decreased expression of others. Thus, a gene not modulated by the test compound (the compound used in contacting the genes or cell containing them) is not considered a member of the set.

Thus, the present invention relates to a gene set wherein expression of each member of said gene set is modulated as a result of contacting said gene set with a compound of the invention. In specific embodiments, expression of each member of said gene set is increased as a result of said contacting or is decreased as a result of said contacting. In another preferred embodiment, the gene set is present in a cell. Such a gene set will commonly be related to a specific disease process, such as a set of genes all of which are modulated by a compound of the invention wherein such compound has a specific therapeutic effect, such as being an anti-neoplastic agent.

The present invention also relates to a method for ameliorating cancer or tumor metastasis in a mammal comprising administering to said mammal an effective amount of a compound of the invention. Especially contemplated are uses of the compounds of Table 1. In selected embodiments, said cancer is a sarcoma or said cancer is a carcinoma. Specific cancers contemplated by the methods of the invention include, but are not limited to, one or more of colon cancer, adenocarcinoma, rectal cancer, colorectal cancer, breast cancer, lung cancer, ovarian cancer, adenomatous polyposis, and hepatocellular carcinoma.

The invention also provides convenient methods for the synthesis of compound of Formula I, according to the general synthetic pathway presented in Scheme 1. The starting sulfonyl chlorides 1 can be obtained by direct chlorosulfonylation of the corresponding aromatic ring system or by chlorination of an appropriate sulfonic acid derivative. Compounds 1 are reacted with 6 or 7-membered cyclic amines to give secondary sulfonamides 2. Compounds 2 can be additionally transformed into derivatives 3 which in some cases serve as prodrugs with modified physico-chemical and pharmacological properties such as solubility in water, modified protein binding properties, stability in plasma, toxicity, and others.

EXAMPLES

Most of the compounds disclosed herein were prepared from the corresponding sulfonyl chloride derivatives according to the general synthetic pathway presented in Scheme 1.

Scheme 1

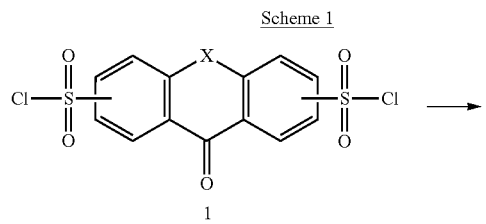

1

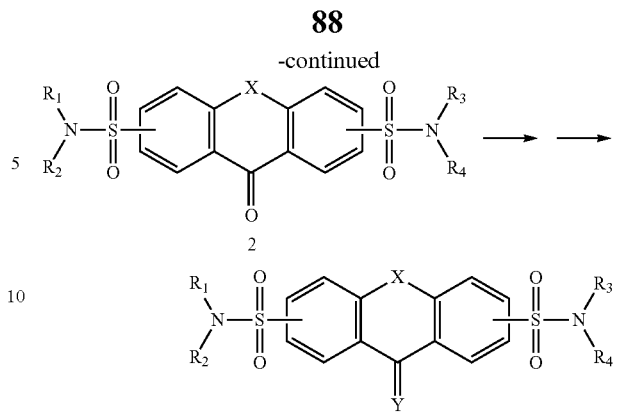

The following Schemes and Examples are intended as an illustration of and not a limitation upon the scope of the invention as defined in the appended claims.

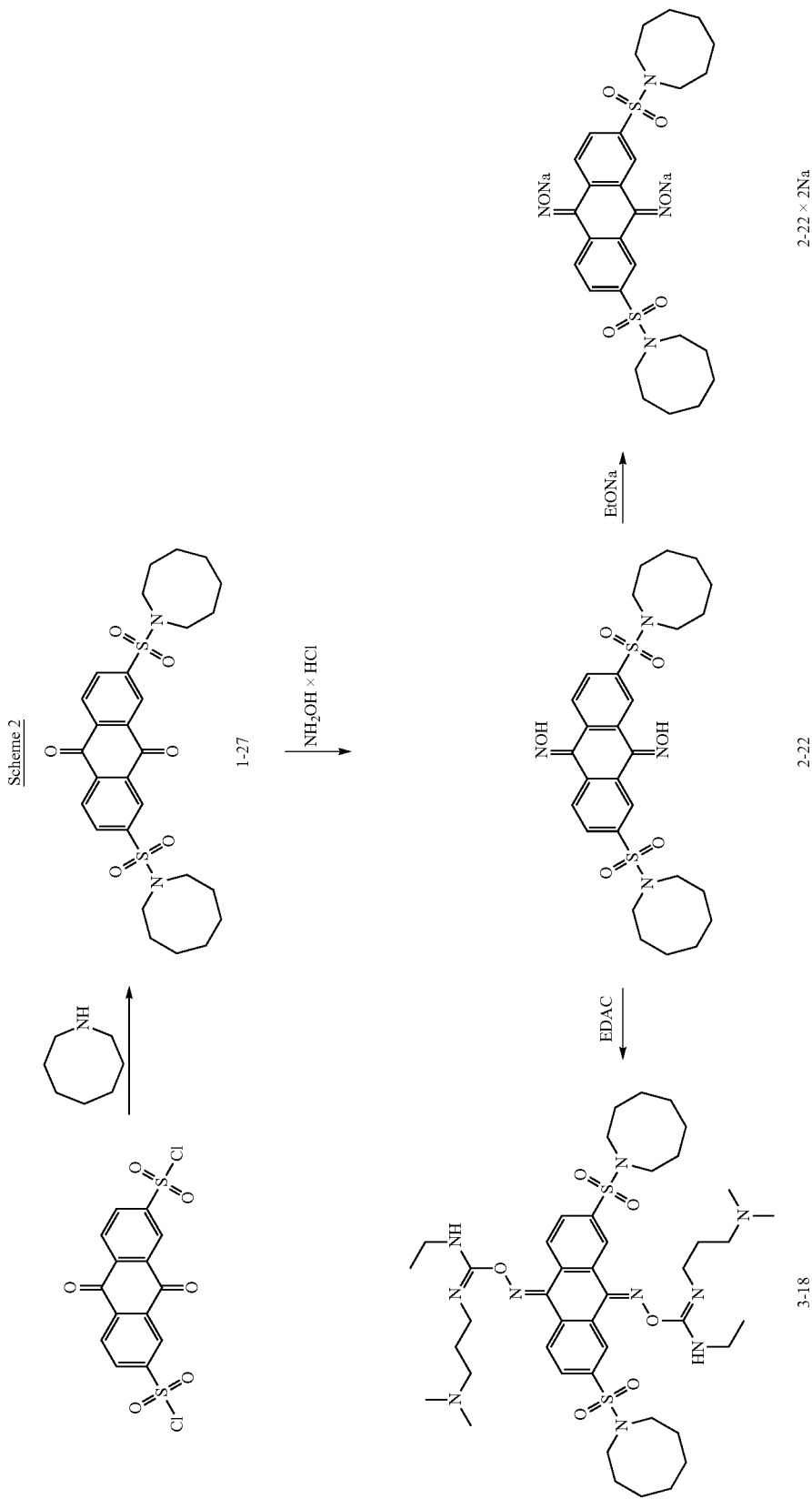

Example 1

2,7-bis(azocan-1-ylsulfonyl)anthracene-9,10-dione (1-27)

Anthraquinone-2,7-disulfonylchloride (1215 mg, 3 mmole) was dissolved in 100 mL DCM. The solution was cooled to −50° C. To this solution was added 1 mL (8 mmole) of heptamethyleneimine, followed by 1 mL of diisopropylethylamine. The reaction mixture was stirred at room temperature for 4 hrs. Solvent was evaporated and the residue was treated with 1N HCl, filtered off, washed with water and dried. Crude material was crystallized from chloroform-hexane to give 1.014 g (91%) of yellow compound 1-27. $H^1$-NMR (CDCl$_3$): 8.70 (2H, d, C1 and C8), 8.47 (2H, d, C4 and C5), 8.22 (2H, dd, C3 and C6), 3.22 (8H, m), 1.70 (20H, m).

Example 2

2,7-bis(azocan-1-ylsulfonyl)anthracene-9,10-dione dioxime (2-22)

The product from Example 1 (1.0 g, 1.706 mmole), 5 mL of pyridine and hydroxylamine hydrochloride (1.5 g, 21.5 mmole) was stirred at 95° C. for 36 hrs. Pyridine was evaporated and the residue was stirred with 1 N HCl (50 mL) for several minutes. White product was collected by filtration, washed with water and dried. Crude material was then crystallized from DCM-hexane to give 970 mg (97%) of a white compound 2-22. $H^1$NMR (CDCl$_3$): 9.05 (1H, dd), 8.75 (1H, dd), 8.35 (1H, dd), 8.05 (1H, dd), 7.90 (2H, m), 3.20 (8H, m), 1.70 (20H, m).

Example 3

2,7-bis(azocan-1-ylsulfonyl)anthracene-9,10-dione dioxime disodium salt (2-22×2Na)

A mixture of compound 2-22 (620 mg, 1.0 mmole), 35 mL of DCM and 2.2 mL of 1M sodium ethoxide in ethanol was stirred with heating until a clear solution was formed. To the solution was added 100 mL of ether and the mixture was sonicated for 5 min. Yellow solid of product was collected by filtration, washed with ether and dried to give 660 mg (100%) of the title compound.

Example 4

9,10-bis(N'-(3-(dimethylamino)propyl)-N-ethylcarbamimidoyloxyimino)-2,7-bis(azocan-1-ylsulfonyl)-9,10-dihydro-anthracene tetrahydrochloride (3-18)

Compound 2-22 (442 mg, 0.75 mmole), 4 mL of anhydrous chloroform and 400 mg of EDAC were stirred at 60° C. for 1 hr. The reaction mixture was condensed and chromatographed by HPLC. Combined fractions containing the desired product (MH$^+$=899) were acidified by addition of 5 mL of 1N HCl and evaporated to dryness. The product was dissolved in distilled water and lyophilized to give 530 mg (68%) of white title compound.

Scheme 3

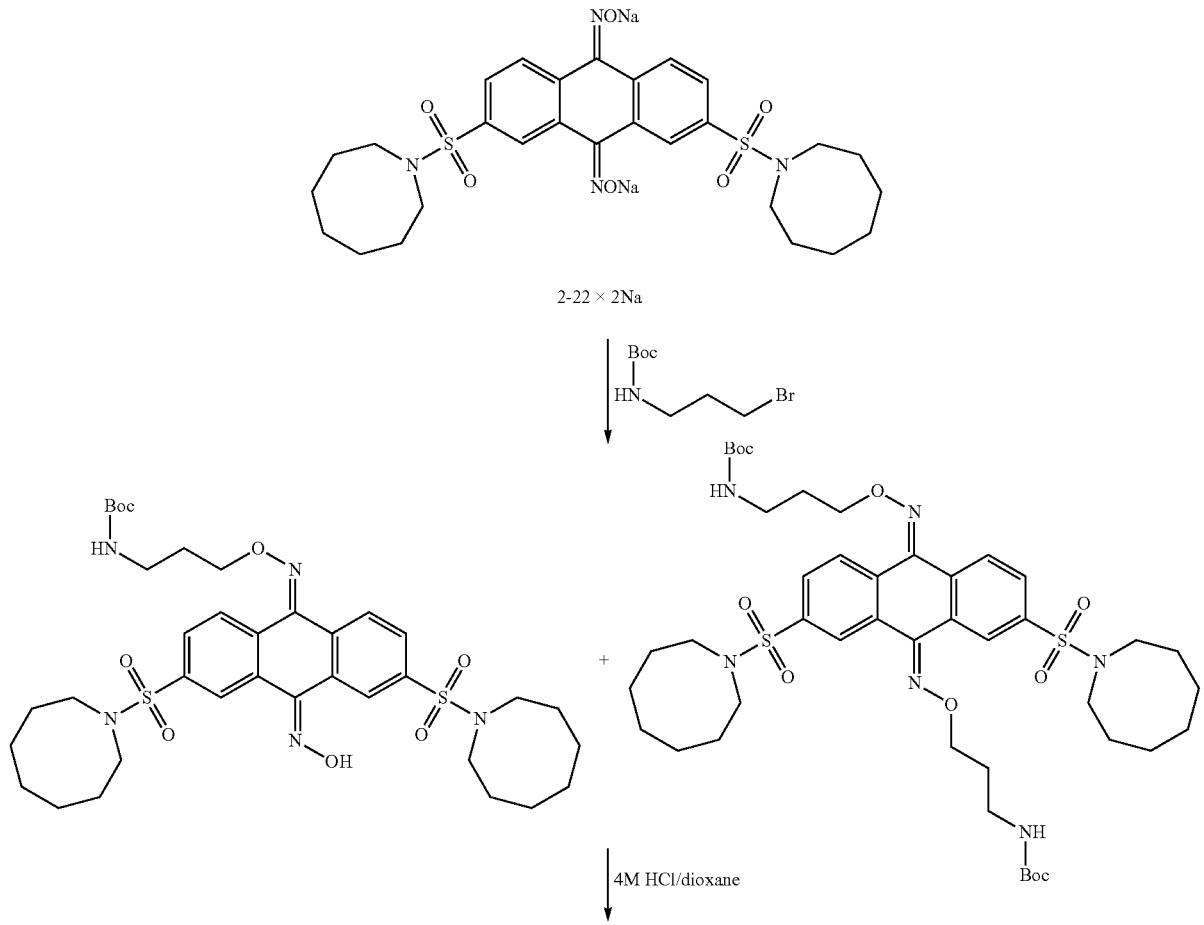

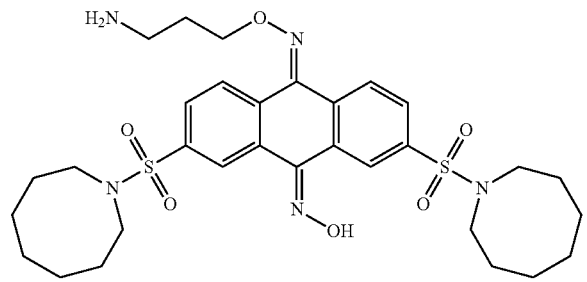

3-28

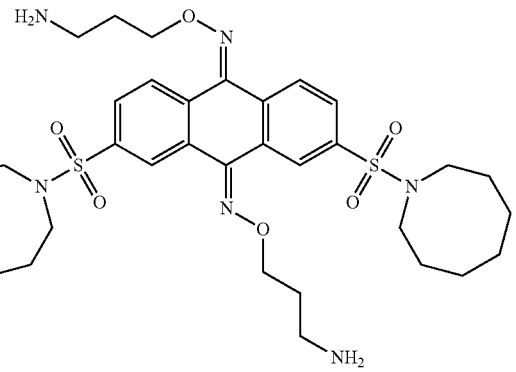

3-24

Example 5

9,10-bis[(3-aminopropyl)oxyimino]-2,7-bis(azocan-1-ylsulfonyl)-9,10-dihydro-anthracene (3-24)

To a solution of compound 2-22×2Na (320 mg, 0.5 mmole) in DMSO (2 mL) tert-butyl 3-bromopropylcarbamate (180 mg, 0.75 mmole) was added and the mixture was stirred at room temperature for 1 h. Water was added to the reaction mixture and precipitated products were extracted with ethyl acetate. The extract was dried with sodium sulfate, evaporated, and the residue was stirred with 4N HCl/dioxane (5 mL) for 1 hr. Solvent was evaporated and the residue was dissolved in methanol and purified by preparative HPLC. Fractions containing the major product were acidified with hydrochloric acid and evaporated. The residue was dissolved in water and lyophilized to provide the title compound as dihydrochloride salt (170 mg, 44% yield for 2 steps). MS 703 (MH⁺).

Example 6

10-(3-aminopropyl)oxyimino-9-hydroxyimino-2,7-bis(azocan-1-ylsulfonyl)-9,10-dihydro-anthracene (3-24)

The title compound was isolated as a second major product from Example 5. Yield: 20% after 2 steps. MS 646 (MH⁺).

Scheme 4

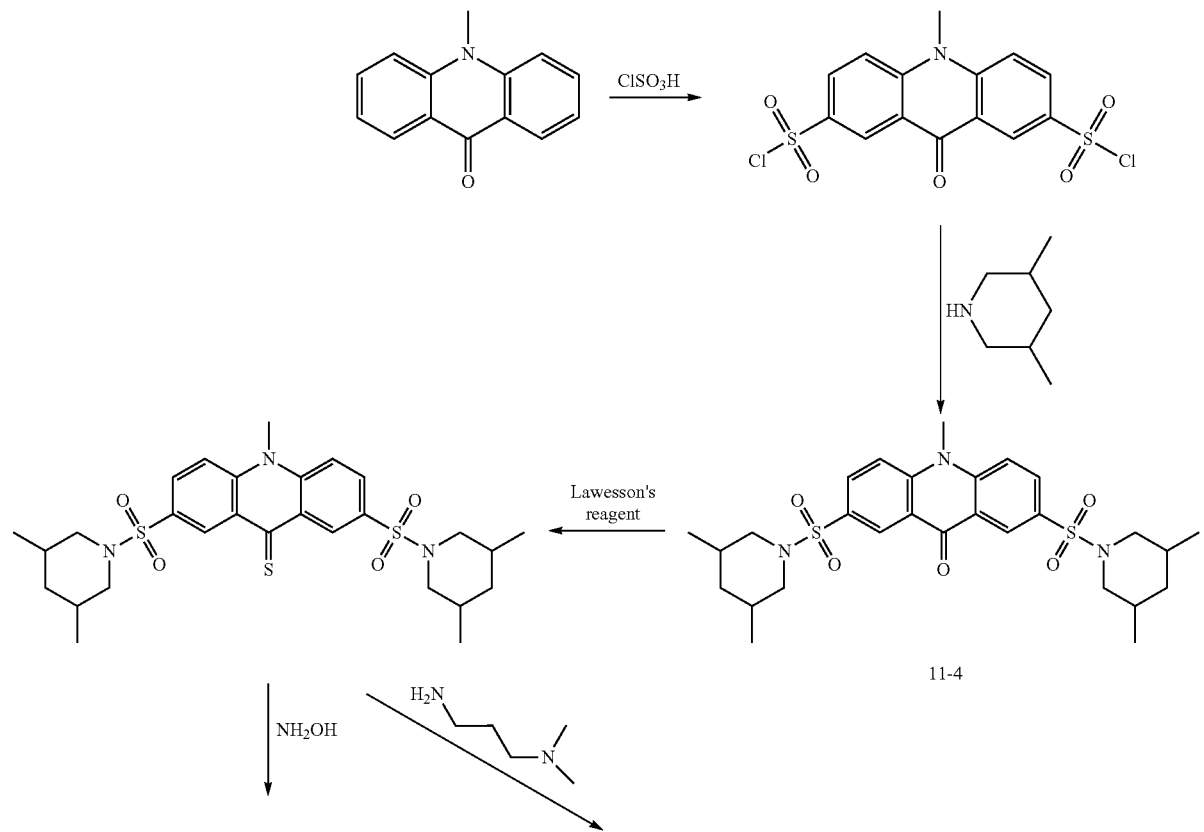

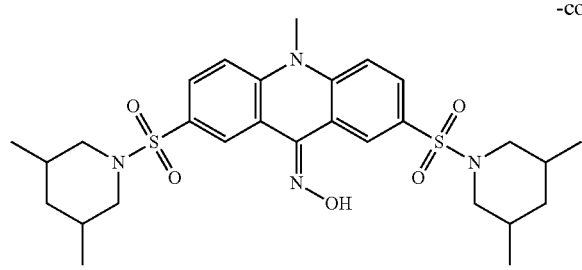

12-4

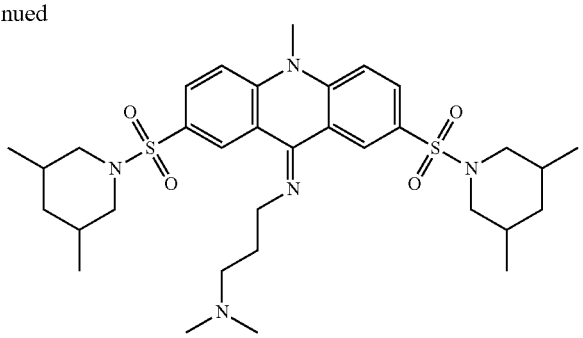

12-5

Example 7

10-methyl-9-oxo-9,10-dihydroacridine-2,7-disulfonyl dichloride

A mixture of 10-methylacridin-9(10H)-one (4.2 g, 20 mmole) and chlorosulfonic acid (100 mL, 1.5 mole) was heated at reflux for 5 hours. Reaction mixture was then condensed, cooled down to room temperature and poured carefully on 500 g of ice. The yellow precipitate of product was collected by filtration, washed with water and dried to provide 8.1 g of the title compound. This material was used for next step without purification.

Example 8

2,7-bis(3,5-dimethylpiperidin-1-ylsulfonyl)-10-methylacridin-9(10H)-one (11-4)

To a solution of 10-methyl-9-oxo-9,10-dihydroacridine-2,7-disulfonyl dichloride from Example 7 (810 mg, 2 mmole) in THF (20 mL) was added 3,5-dimethylpiperidine (2 mL, 15 mmole) and the reaction mixture was stirred at room temperature for 6 hours. Solvent was evaporated and the residue was treated with 1 N HCl (50 mL) and stirred for 10 minutes. Yellow product was collected by filtration, washed with water and methanol and dried. Crude material was crystallized from chloroform-ethanol to provide 900 mg (80%) of yellow 11-4. MS 560 (MH$^+$).

Example 9

2,7-bis(3,5-dimethylpiperidin-1-ylsulfonyl)-10-methylacridine-9(10H)-thione

A mixture of compound 11-4 (560 mg, 1 mmole), anhydrous toluene (10 mL) and Lawesson's reagent (820 mg, 2 mmole) was refluxed for 4 hrs. Toluene was removed by evaporation. To the residue methanol (20 mL) was added, stirred for few minutes at room temperature and the product was collected by filtration and dried to give 500 mg of the title compound. MS 576 (MH$^+$).

Example 10

2,7-bis(3,5-dimethylpiperidin-1-ylsulfonyl)-9-hydroxyimino-10-methyl-(9H,10H)-acridine (12-4)

To a solution of 2,7-bis(3,5-dimethylpiperidin-1-ylsulfonyl)-10-methylacridine-9(10H)-thione (290 mg, 0.5 mmole) in pyridine (5 mL) was added hydroxylamine hydrochloride (210 mg, 30 mmole) and the mixture was stirred at 100° C. for 8 hrs. Solvent was removed and the residue was treated with water to remove excess of hydroxylamine. Crude material was crystallized from methanol-water to give 245 mg (85%) of the title compound. MS 575 (MH$^+$).

Example 11

2,7-bis(3,5-dimethylpiperidin-1-ylsulfonyl)-9-(3-dimethylaminopropyl)imino-10-methyl-(9H,10H)-acridine (12-5)

A mixture of 2,7-bis(3,5-dimethylpiperidin-1-ylsulfonyl)-10-methylacridine-9(10H) thione (145 mg, 0.25 mmole), pyridine (5 mL) and dimethylaminopropylamine (0.125 mL, 1 mmole) was stirred at 100° C. for 4 hrs. Solvent was partially evaporated and reaction product was precipitated by addition of methanol. Precipitate was collected by filtration, washed with methanol and dried to give 137 mg (85%) of the title compound. MS 644 (MH$^+$).

Scheme 5

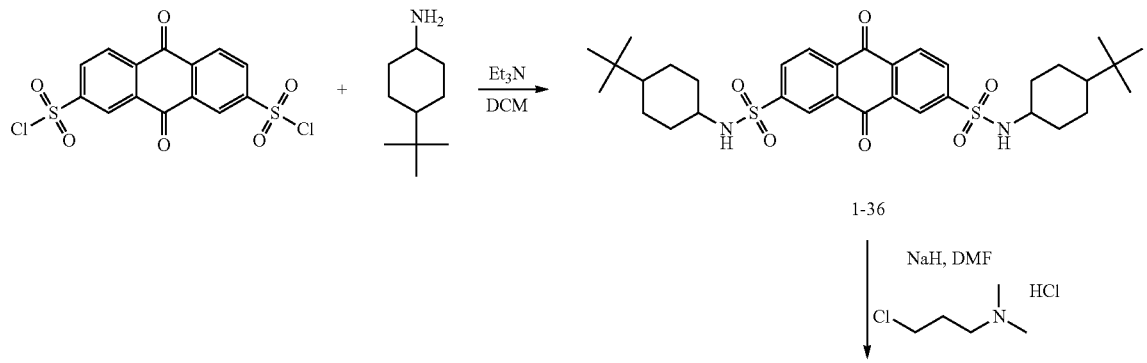

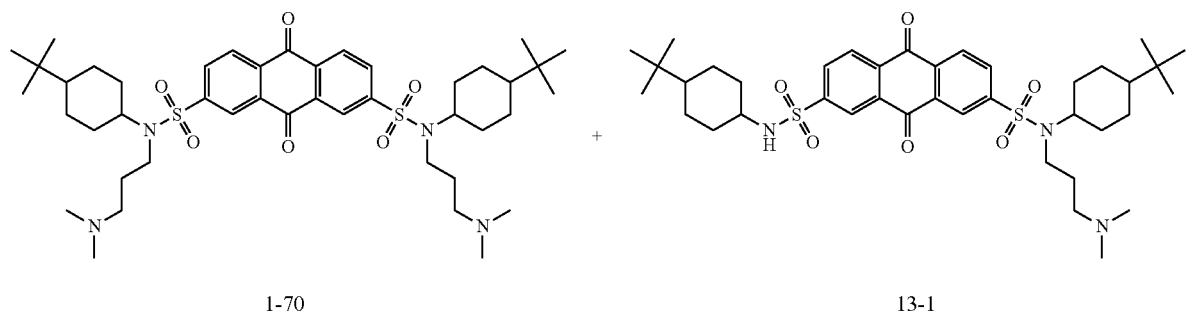

1-70     13-1

Example 12

$N^2,N^7$-bis(4-tert-butylcyclohexyl)-9,10-dioxo-9,10-dihydroanthracene-2,7-disulfonamide (1-36)

Anthraquinone-2,7-disulfonylchloride (10 g, 24.7 mmol)) was dissolved in 200 mL DCM. The solution was cooled to −50° C. To this solution was added 4-tert-butylcyclohexanamine (8.43 g, 54 mmol), followed by triethyl amine (8.6 ml, 61.7 mmol). The reaction mixture was stirred at room temperature for 4 hrs. Solvent was evaporated and the residue was treated with MeOH, filtered off, and dried to obtain 15 g (95%) of the product (1-36) as yellow powder.

Example 13

$N^2,N^7$-bis(4-tert-butylcyclohexyl)-$N^2$-(3-(dimethylamino)propyl)-9,10-dioxo-9,10-dihydroanthracene-2,7-disulfonamide (13-1) and $N^2,N^7$-bis(4-tert-butylcyclohexyl)-$N^2,N^7$-bis(3-(dimethylamino)propyl)-9,10-dioxo-9,10-dihydroanthracene-2,7-disulfonamide (1-70)

To an ice cold solution of the sulfonamide (1-36, 6.82 g, 10.61 mmol) in anhydrous DMF (100 ml) under argon was added NaH (95.0%, 697 mg, 27.58 mmol). The solution was stirred for 5 min, and then 3-chloro-N,N-dimethylpropan-1-amine hydrochloride (2.18 g, 13.8 mmol) was added. After 10 min, the reaction mixture was transferred to a pre heated oil bath at 40° C. and stirred for 3 days. LCMS showed the presence of monoalkylated and bisalkylated products (ratio, 65:25) together with unreacted starting material. After cooling, 1N NaOH was added to the reaction mixture and extracted with ethyl acetate. The organic phase was dried over anhydrous magnesium sulfate and the filtrate was evaporated under reduced pressure. The crude mixture was purified by silica gel column chromatography. The unreacted starting material was recovered when the column was eluted with 40° A) EtOAc in hexane. Pure monoalkylated product (13-1, LCMS, MS 728.0 (MH+)) was obtained when eluted using EtOAc alone and the bisalkylated product (1-70, LCMS, MS 813.2 (MH+)) was isolated with 5% triethylamine in EtOAc as the eluent. The fractions collected were evaporated under reduced pressure to dryness to get 13-1 (3.02 g, 53%) and 1-70 (1.10 g, 17%).

Scheme 6

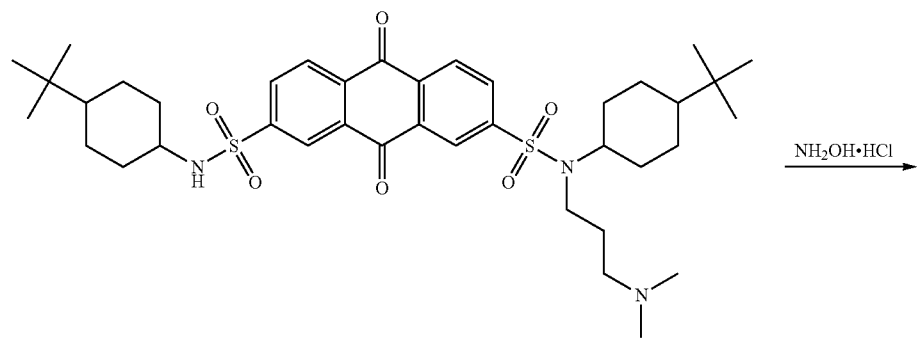

13-1

$NH_2OH \cdot HCl$

-continued

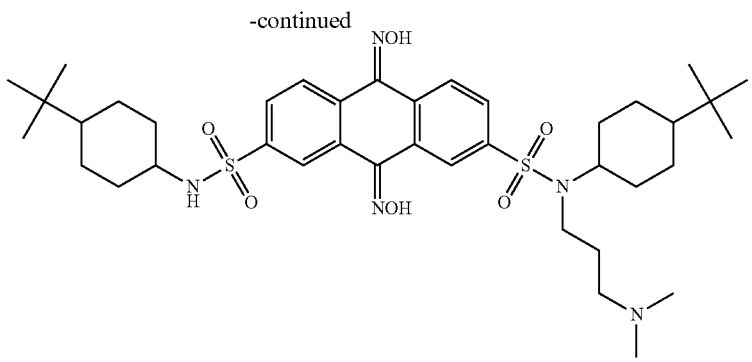

6-1

Example 14

N²,N⁷-bis(4-tert-butylcyclohexyl)-N²-(3-(dimethyl-amino)propyl)-9,10-bis(hydroxyimino)-9,10-dihydroanthracene-2,7-disulfonamide (6-1)

The dioxime (6-1) was prepared following the general procedure using monoalkylated sulfonamide (13-1, 2 g, 2.7 mmol), excess hydroxylamine hydrochloride (2.7 g, 27.5 mmol) and pyridine (50 ml) at 95° C. for 36 hrs. After cooling, excess hydroxylamine was removed by filtration, washed with pyridine and the filtrate was evaporated under reduced pressure to dryness. To this was added excess of aqueous 1N HCl, the oxime was precipitated out, filtered to collect the colorless precipitate and dried. The oxime (6-1) was further purified by crystallization or HPLC to get it as a colorless HCl salt (1.42 g, 65%).

¹H NMR (400 MHz, DMSO-d6) δ: 13.04-13.01 (m, 1H), 12.94-12.89 (m, 1H), 10.48 (br s, 1H), 9.18-9.07 (m, 1H), 8.87-8.78 (m, 1H), 8.40-7.78 (m, 4H), 3.75-3.05 (m, 16H), 2.72 (s, 6H), 1.96-0.76 (m, 28H).

Example 15

N²,N⁷-bis(4-tert-butylcyclohexyl)-N²,N⁷-bis(3-(dimethylamino)propyl)-9,10-bis(hydroxyimino)-9,10-dihydroanthracene-2,7-disulfonamide (2-65)

Following the general procedure described above, the dioxime (2-65) was prepared as HCl salt (0.710 g, 63%) from the corresponding anthraquinone derivative (1-70, 1 g, 1.23 mmol), excess hydroxylamine hydrochloride (1.2 g, 12.3 mmol) and pyridine (25 ml) at 95° C. for 36 hrs.

¹H NMR (400 MHz, DMSO-d6) δ: 13.09-13.07 (m, 1H), 12.98-12.95 (m, 1H), 9.14-9.08 (m, 1H), 8.89-8.82 (m, 1H), 8.35-7.92 (m, 4H), 3.75-3.04 (m, 16H), 2.72-0.77 (m, 46H).

What is claimed is:

1. A method of decreasing beta-catenin levels in tumor cells in a mammal comprising administering to said mammal an effective amount of a compound having the structure of Formula I

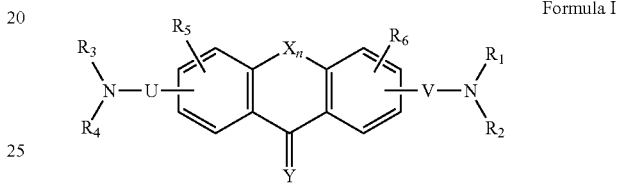

Formula I wherein n=1-2 and wherein when n=1, X is selected from $CH_2$, O, CO, and $C=NOR_A$ and wherein when n=2, $X=CH_2$, Y is O, S, $NOR_A$, or $NR_A$, wherein U and V are each O=S=O, wherein $R_A$ is selected from H, alkyl, heteroalkyl, alkenyl, alkynyl, cycloalkyl, —C(=O)RB, —C(=O)$OR_B$, —C(=O)$NR_BR_C$, —C(=$NR_B$)RC, —$NR_BR_C$, heterocycloalkyl, aryl or polyaromatic, heteroaryl, arylalkyl and alkylaryl, wherein each of said $R_B$ and $R_C$ is independently H, alkyl, or heteroalkyl, $R_1$, $R_2$, $R_3$, and $R_4$ are each independently selected from H, alkyl, heteroalkyl, cycloalkyl, arylcycloalkyl, alkenyl, alkynyl, aryl, heteroaryl, heterocycloalkyl, and each of said $NR_1R_2$ and $NR_3R_4$ can independently combine to form a heterocycloalkyl, $R_5$ and $R_6$ are each independently selected from H, OH, SH, alkoxy, thioalkoxy, alkyl, halogen, CN, $CF_3$, $NO_2$, $COOR_D$, $CONR_DR_E$, $NR_DR_E$, $NR_DCOR_E$, $NR_DSO_2R_E$, and $NR_F-CONR_DR_E$;

wherein $R_D$, $R_E$ and $R_F$ are independently H, alkyl, heteroalkyl, aryl, arylalkyl, heteroaryl, heteroarylalkyl, cycloalkyl, or heterocycloalkyl; provided that is X is O, Y is O and U and V are both O=S=O, then $NR_1R_2$ and $NR_3R_4$ are not identical then $R_1$ and $R_3$ are each independently selected from H and lower alkyl, and wherein $R_2$ and $R_4$ are each independently selected from lower alkoxy(loweralkyl), di(lower)alkylamino (lower)alkyl, halobenzyl, morpholino(lower)alkyl, or $NR_1R_2$ and $NR_3R_4$ are independently piperidino, morpholino, piperazino, N-phenylpiperazino, ethylamino, or substituted glycine, and wherein if X is $(CH_2)_2$, and Y is O or NOH, then none of $R_1$, $R_2$, $R_3$, and $R_4$ is methyl, and wherein if X is CO and Y is O, then $NR_1R_2$ and $NR_3R_4$ are not identical, and wherein $R_1$, $R_2$, $R_3$, and $R_4$ are each independently selected from methyl, ethyl, hydroxy-$C_1$-$C_3$-alkyl, SH, RO, COOH, SO, $NH_2$, and phenyl or wherein one or both of non-identical $NR_1R_2$ and $NR_3R_4$ is unsubstituted piperidino, N-methylpiperazino or N-methyl homopiperazino, wherein said unsubstituted piperidino, N-methylpiperazino or N-methylhomopiperazino $NR_1R_2$ and $NR_3R_4$ moieties are not identical, and wherein when X is C=O or C=NOH, Y is O or NOH, and one of $R_1$ or $R_2$ and one of $R_3$ or $R_4$ is phenyl then the other of R1 or $R_2$ and $R_3$ or $R_4$ is not H or alkyl, or a pharmaceutically acceptable salt, ester, amide, stereoisomer or geometric isomer thereof.

2. The method of claim 1, wherein X is $CH_2$ and n=1 or 2 and Y is O or S.

3. The method of claim 1, wherein X is $CH_2$ and n=1 or 2 and Y is $NOR_A$, or $NR_A$.

4. The method of claim 1, wherein X is O, and Y is O or S.

5. The method of claim 1, wherein X is O, and Y is $NOR_A$, or $NR_A$.

6. The method of claim 1, wherein X is CO and Y=O.

7. The method of claim 1, wherein the compound has formula II

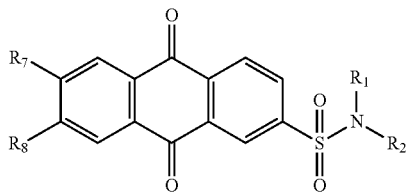

Formula II wherein $R_7$ and $R_8$ are independently selected from H and $SO_2NR_3R_4$ and one of $R_7$ or $R_8$ is hydrogen and the other substituents have the meanings as defined in claim 1.

8. The method of claim 7, wherein $R_1$, $R_2$, $R_3$, and $R_4$ are each independently selected from H, alkyl, cycloalkyl, alkenyl, and alkynyl.

9. The method of claim 7, wherein $NR_1R_2$ and $NR_3R_4$ are each independently a 6- to 15-membered heterocycloalkyl.

10. The method of claim 1, wherein X is CO and Y is $NOR_A$ or $NR_A$.

11. The method of claim 1, wherein X is C=$NOR_A$ and Y is O.

12. The method of claim 1, wherein X is C=NORA and Y is NORA.

13. The method of claim 1, wherein said compound has Formula III

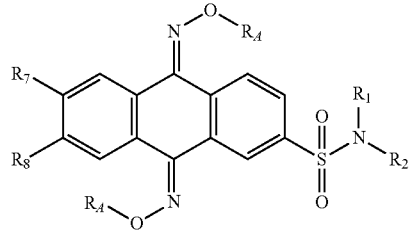

Formula III wherein $R_7$ and $R_8$ are independently selected from H and $SO_2NR_3R_4$, wherein one of $R_7$ and $R_8$ is hydrogen and the other substituents have the meanings as defined in claim 1.

14. The method of claim 13, wherein $R_1$, $R_2$, $R_3$, and $R_4$ are each independently selected from H, alkyl, cycloalkyl, alkenyl, or alkynyl.

15. The method of claim 1, wherein said compound has the following formula:

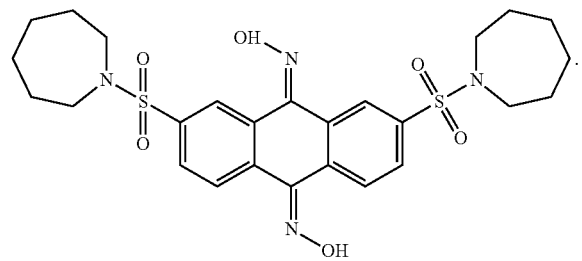 [SMILES: O=S(=O)(c1ccc2c(c1)C(=NO)c1cc(S(=O)(=O)N3CCCCCC3)ccc1C2=NO)N1CCCCCC1]

* * * * *